US006006752A

United States Patent [19]
Sykes

[11] Patent Number: 6,006,752
[45] Date of Patent: Dec. 28, 1999

[54] MIXED CHIMERISM AND TOLERANCE

[75] Inventor: Megan Sykes, Boston, Mass.

[73] Assignee: The General Hospital Corporation, Boston, Mass.

[21] Appl. No.: 08/855,705

[22] Filed: May 8, 1997

Related U.S. Application Data

[60] Provisional application No. 60/017,099, May 9, 1996.

[51] Int. Cl.⁶ .......................... A61B 19/00; A61K 35/28
[52] U.S. Cl. .......................................... 128/898; 424/93.1
[58] Field of Search ................................ 623/11, 12, 66; 128/898; 424/93.1, 93.21, 93.7, 93.71

[56] References Cited

U.S. PATENT DOCUMENTS

| | | | |
|---|---|---|---|
| 5,597,563 | 1/1997 | Beschorner | 424/93.7 |
| 5,806,529 | 9/1998 | Reisner . | |
| 5,876,708 | 3/1999 | Sachs . | |

OTHER PUBLICATIONS

W. Beschorner et al., "Recruitment of Semiallogeneic Dendritic Cells to The Thymus During Post–Cyclosphorine Thymic Regeneration", *Transplantation*, vol. 60, No. 11, pp. 1326–1330, 1995.

Reisner et al., "Bone Marrow Transplantation Across HLA Barriers By Increasing The Number Of Transplanted Cells", *Immunology Today*, vol. 16, No. 9, pp. 437–440, 1995.

Kahan, "Drug Therapy, Cyclosporine" *NE J. Medicine* 321(25):1725–1738 (1989).

Fung et al., "Conversion of Liver Allograft Recipients From Cyclosporine to FK 506–Based Immunosuppression: Benefits and Pitfalls" *Transplantation Proc.* 23(1):14–21 (1991).

Makowka et al., The Development of Brequinar as an Immunosuppressive Drug for Transplantation *Immunological Reviews* 136:51–70 (1993).

Sykes et al., "Xenograft Tolerance" *Immunological Reviews* 141:246–276 (1994).

Starzl et al., "The Biological Basis of and Strategies for Clinical Xenotransplantation" *Immunological Reviews* 141:213–244 (1994).

Ramshaw et al., "High levels of engraftment with a single infusion of bone marrow cells into normal unprepared mice", Biol. of Blood and Marrow Transpl. 1:74–80 (1995).

Shizuru et al., "Transplantation of purified hematopoietic stem cells: Requirements for overcoming the barriers of allogeneic engraftment", Biol. of Blood and Marrow Transpl. 2:3–14 (1996).

Anasetti et al., Effect of HLA compatibility on engraftment of bone marrow transplants in patients with leukemia or lymphoma, 1989, vol. 320:197–204. New England Journal of Medicine.

Aversa et al., Successful engraftment of T–cell–depleted haploidentical "three–loci" incompatible transplants in leukemia patients by addition of recombinant human granulocyte colony–stimulating factor–mobilized peripheral blood progenitor cells to bone marrow inoculum, 1994, vol. 84:3948–3955, Blood.

Bachar–Lustig et al., Megadose of T cell–depleted bone marrow overcomes MHC barriers in sublethally irradiated mice, 1995, vol. 1:1268–1273, Nature Med.

Brecher et al., Special proliferative sites are not needed for seeding and proliferation of transfused bone marrow cells in normal syngeneic mice, 1982, vol 79:5085–5087, PNAS USA.

Lee et al., Natural killer cells weakly resist engraftment of allogeneic long–term multilineage–repopulating hematopoietic stem cells, 1996, vol. 61:125–132, Transplantation.

(List continued on next page.)

*Primary Examiner*—David J. Isabella
*Attorney, Agent, or Firm*—Fish & Richardson P.C.

[57] ABSTRACT

A method of inducing tolerance without whole body irradiation.

53 Claims, 5 Drawing Sheets

OTHER PUBLICATIONS

O'Reilly et al., Transplantation of marrow depleted T cells by soybean lectin agglutination and E–rosette deletion: major histocompatibility complex–related graft resistance in leukemic transplant recipients, 1985, vol; 17:455–459, Transplant. Proc.

Stewart et al., Long–term engraftment of normal and post–5–fluoracil murine marrow into normal nonmyeloablated mice, 1993, vol. 81:2566–2571, Blood.

Tomita et al., Myelosuppressive conditioning is required to achieve engraftment of pluripotent stem cells contained in moderate doses of syngeneic bone marrow, 1994, vol 83: 939–948, Blood.

Tomita et al., Additional mAB injections can replaced thymic irradiation to allow induction of mixed chimerism and tolerance in mice receiving bone marrow transplantation after conditioning with anti–T cell mABs and Gy whole body irradiation, 1996, vol. 61:469–477, Transplantation.

Tomita et al., Mechanism by which additional monoclonal antibody injections overcome the requirement ofr thymic irradiation to achieve mixed chimerism in mice receiving bone marrow transplantation after conditioning with anti–T cell mABs and 3 Gy whole body irradiation, 1996, vol. 61:477–485, Transplantation.

MIXED CHIMERISM AND TOLERANCE

This application is a continuation-in-part of U.S. provisional application Ser. No. 60/017,099 filed on May 9, 1996, and which is hereby incorporated by reference.

BACKGROUND OF THE INVENTION

The invention relates to tissue and organ transplantation.

SUMMARY OF THE INVENTION

The invention provides methods of inducing tolerance to foreign antigens. The methods feature preparative regimens which minimize or eliminate the need for hematopoietic space-creating irradiation, especially, preparative whole body irradiation. In particular, it has been discovered that the administration of a relatively large number of stem cells, combined with the creation of thymic space, can allow the induction of tolerance without the need for whole body irradiation (WBI).

Accordingly, the invention features a method of inducing tolerance in a recipient mammal of a first species to a graft from a donor mammal of a second species. The method includes: introducing, e.g., by intravenous injection, into the recipient mammal, hematopoietic stem cells; and preferably, implanting the graft in the recipient. The hematopoietic cells are believed to prepare the recipient for the graft that follows, by inducing tolerance at both the B-cell and T-cell levels.

The recipient mammal can be, by way of example, a human. The donor mammal can be, by way of example, a swine, e.g., a miniature swine. The graft is preferably from a discordant species. The graft preferably expresses a major histocompatibility complex (MHC) antigen, preferably a class II antigen. In particularly preferred embodiments the recipient is a primate, e.g., a human, and the donor is a swine, e.g., a miniature swine.

As is discussed elsewhere herein, the inventors have discovered that this method can be practiced without the administration of hematopoietic space-creating irradiation, e.g., whole body irradiation. Whole body irradiation is often used in the art to create hematopoietic space and thus promote engraftment, chimerism, and tolerance. The need for hematopoietic space-creating irradiation can be reduced or entirely eliminated by the inclusion of one or more of the following steps in the method:

(1) Administering a sufficiently large number of donor hematopoietic cells to the recipient such that, donor stem cells engraft, give rise to mixed chimerism, and induce tolerance, preferably the stem cells are administered either in combination with one or more of the treatments disclosed herein, e.g., (2), (3), or (4) described immediately below;

(2) Administering hematopoietic space creating antibodies or drugs to the recipient. E.g., administering an inhibitor of cell proliferation, e.g., DSG, or an anti-metabolite, e.g. brequinar, or an anti-T cell antibody, e.g., one or both of an anti-CD4 or anti-CD8 antibody.

(3) providing treatments (other than whole body irradiation) which promote engraftment and the formation of mixed chimerism by enhancing the ability of donor cells to compete with host bone marrow cells, e.g., administering stromal cells or administering donor specific growth factors or cytokines, e.g., where the donor is a miniature swine, administering one or more of swine SCF, swine IL-3, or swine GM-SCF, to the recipient.

(4) creating thymic space in the recipient, e.g., by irradiating the thymus of the recipient, e.g., by administering between 100 and 1,000, more preferably between 300 and 700, e.g., 700 rads, of thymic irradiation, or by administering anti-T cell antibodies in sufficient dose to inactivate thymocytes. Other methods for the creation of thymic space include: the administration of steroids, corticosteroids, brequinar, or an immune suppressant chemical or drug, e.g., rapamycin, cyclosporin, or FK506. Treatment to create thymic space should be administered, or at least begun, prior to the administration of hematopoietic stem cells. An effective treatment should deplete single positive thymocytes to an extent that engraftment and the formation of mixed chimerism is optimized in the absence of the creation of hematopoietic space, e.g., hematopoietic space created by whole body irradiation. In preferred embodiments the subject's single positive thymocytes are depleted by at least 20, 40, 60, or 80%. Treatments which result in between 10 and 90% depletion are preferred. The length of the treatment will vary with dosage and the effectiveness of the agent but will generally be less than 60, 30, or 15 days. The treatment should last at least 7, and more preferably 10, or 14 days in length. In preferred courses of treatment, e.g., the administration of an immunosuppressive chemical or drug, e.g., cyclosporine, should last between 7 and 30 days. The treatment, e.g., the administration of cyclosporin, should be started at a time such that it is completed prior to the administration of stem cells. Administration of the agent should be on a daily basis or as needed to maintain a level of the agent which allows the desired level of depletion. A particularly preferred treatment is the administration of an immunosuppresive chemical, e.g., cyclosporin, for more than 7 and less than 30 days. A useful regimen in rodents is 20 mg/kg/day cyclosporin for 14 days ending on the third day before administration of stem cells.

Thus, in preferred embodiments a quantity of hematopoietic stem cells sufficient to induce tolerance, without the need for hematopoietic space-creating irradiation, is administered to the recipient. In preferred embodiments the number of donor hematopoietic cells is at least twice, is at least equal to, or is at least 75, 50, or 25% as great as, the number of bone marrow cells found in an adult of the recipient species. In preferred embodiments the number of donor hematopoietic stem cells is at least twice, is at least equal to, or is at least 75, 50, or 25% as great as, the number of bone marrow hematopoietic stem cells found in an adult of the recipient species. In the case where an inbred population of the donor species exists, e.g., where the donor species is miniature swine, the number of available donor cells is not limited to the number of cells which can be obtained from a single animal. Thus, in such cases, the donor cells administered to the recipient can come from more than one, e.g., from two, three, four, or more animals. As is discussed below the donor stem cells can be provided in two or more separate administrations.

In preferred embodiments, mixed chimerism is induced in the recipient and the state of mixed chimerism is formed in the absence of the induction of hematopoietic space, e.g., in the absence of hematopoietic space created by space creating irradiation, e.g., whole body irradiation.

The number of donor cells administered to the recipient can be increased by either increasing the number of stem cells provided in a particular administration or by providing repeated administrations of donor stem cells.

Repeated stem cell administration can promote engraftment, mixed chimerism, and long-term deletional tolerance in graft recipients. Thus, the invention also includes methods in which multiple hematopoietic stem cell administrations are provided to a recipient. Multiple administration can substantially reduce or eliminate the need for hematopoietic space-creating irradiation. Administrations can be given prior to, at the time of, or after graft implantation. In preferred embodiments multiple administrations of stem cells are provided prior to the implantation of a graft. Two, three, four, five, or more administrations can be provided. The period between administrations of hematopoietic stem cells can be varied. In preferred embodiments a subsequent administration of hematopoietic stem cell is provided: at least two days, one week, one month, or six months after the previous administration of stem cells; when the recipient begins to show signs of host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's , e.g. when the donor specific monoclonal stains less than 1–2% of the cells; or generally, as is needed to maintain a level of mixed chimerism sufficient to maintain tolerance to donor antigen.

One or more post graft-implantation-administrations of donor stem cells can also be provided to minimize or eliminate the need for irradiation. Post graft administration of hematopoietic stem cell can provided: at least two days, one week, one month, or six months after the previous administration of stem cells; at least two days, one week, one month, six months, or at any time in the life span of the recipient after the implantation of the graft; when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's , e.g. when the donor specific monoclonal stains less than 1–2% of the cells; or generally, as is needed to maintain tolerance or otherwise prolong the acceptance of a graft.

When multiple stem cell administrations are given one or more of the administrations can include a number of donor hematopoietic cells which is at least twice, is equal to, or is at least 75, 50, or 25% as great as, the number of bone marrow cells found in an adult of the recipient species; include a number of donor hematopoietic stem cells which is at least twice, is equal to, or is at least 75, 50, or 25% as great as, the number of bone marrow hematopoietic stem cells found in an adult of the recipient species.

In preferred embodiments the method includes inactivating natural killer cells, preferably graft reactive or xenoreactive, e.g., swine reactive, NK cells, of the recipient mammal. This can be accomplished, e.g., by introducing into the recipient mammal an antibody capable of binding to natural killer cells of the recipient mammal. The administration of antibodies, or other treatment to inactivate natural killer cells, can be given prior to introducing the hematopoietic stem cells into the recipient mammal or prior to implanting the graft in the recipient. This antibody can be the same or different from an antibody used to inactivate T cells.

In preferred embodiments the method includes inactivating T cells, preferably graft reactive or xenoreactive, e.g., swine reactive, T cells of the recipient mammal. This can be accomplished, e.g., by introducing into the recipient mammal an antibody capable of binding to T cells of the recipient mammal. The administration of antibodies, or other treatment to inactivate T cells, can be given prior to introducing the hematopoietic stem cells into the recipient mammal or prior to implanting the graft in the recipient. This antibody can be the same or different from an antibody used to inactivate natural killer cells.

One source of anti-NK antibody is anti-human thymocyte polyclonal anti-serum. Preferably, a second anti-mature T cell antibody can be administered as well, which lyses T cells as well as NK cells. Lysing T cells is advantageous for both bone marrow and graft survival. Anti-T cell antibodies are present, along with anti-NK antibodies, in anti-thymocyte anti-serum. Repeated doses of antibodies, e.g., anti-NK or anti-T cell antibodies, may be preferable. Monoclonal preparations can be used in the methods of the invention.

In preferred embodiments the recipient does not receive treatments which stimulate the release of a cytokine by mature T cells. E.g., the recipient should not receive a substance, e.g., a steroid drug, e.g., Prednisone (17,21-dihydroxypregna- 1,4-diene-3,11,20-trione), at a dosage or concentration which stimulates the release of a cytokine by mature T cells in the recipient. Preferably, the recipient is free of such treatment from the time stem cells are first administered until the graft is implanted or until mixed chimerism and tolerance is established.

In preferred embodiments the method includes the administration of a short course of help reducing treatment, e.g., a drug or other chemical agent, which induces tolerance to unmatched class I and/or minor antigens on the graft which is introduced into the recipient. The short course of help reducing treatment, e.g., a short course of high dose cyclosporine, is generally administered at the time at the graft is introduced into the recipient. The duration of the short course of help reducing treatment is approximately equal to or is less than the period required for mature T cells of the recipient species to initiate rejection of an antigen after first being stimulated by the antigen; in more preferred embodiments, the duration is approximately equal to or is less than two, three, four, five, or ten times, the period required for a mature T cell of the recipient species to initiate rejection of an antigen after first being stimulated by the antigen. These methods are described in more detail in co-owned application Ser. No. 08/458,720, filed Jun. 1, 1995, which is hereby incorporated by references. Methods of Ser. No. 08/458,720 can be combined with the methods described herein.

Other preferred embodiments include: the step of introducing into the recipient mammal, donor species-specific stromal tissue, preferably hematopoietic stromal tissue, e.g., fetal liver or thymus. In preferred embodiments: the stromal tissue is introduced simultaneously with, or prior to, the hematopoietic stem cells; the hematopoietic stem cells are introduced simultaneously with, or prior to, the antibody.

Other preferred embodiments include treatments to further inactivate recipient T cells, particularly thymic or lymph node thymocytes or T cells. Thymic or lymph node thymocytes or T cells might otherwise inhibit the engraftment or survival of the administered cells. Such inactivation can be accomplished by one or more of: irradiating the thymus of the recipient mammal with a dose of radiation sufficient to inactivate thymocytes, e.g., 100–1,000, more preferably between 300 and 700, e.g., about 350 or 700 rads of thymic irradiation; administering one or repeated doses of an anti-T cell or anti-thymocyte antibody; or administering to the recipient a short course of an immunosuppressant chemical or drug, as is described herein. Inactivation of thymocytes or T cells can be performed prior to hematopoietic stem cell or graft transplantation. In preferred embodiments the method includes diminishing or inhibiting thymocyte or T cell activity, preferably the activity of thymic or lymph node T cells by administering to the recipient a short course of an immunosuppressive agent, e.g., a chemical or drug, e.g., cyclosporine, sufficient to inactivate thymocytes or T cells, preferably thymic or lymph node T cells. The duration of the short course of immunosuppressive agent is: approximately equal to 30 days; approximately equal to or less than 8–12 days, preferably about 10 days; approximately equal to or less than two, three, four, five, or ten times the 8–12 or 10 day period. The short course can begin: before or at about the time the treatment to induce tolerance is begun, e.g., at about the time stem cells are introduced into the recipient; on the day the treatment to induce tolerance is begun, e.g., on the day stem cells are introduced into the recipient; within 1, 2, 4, 6, 8, 10, or 30 days before or after the treatment to induce tolerance is begun, e.g., within 1, 2, 4, 6, 8, 10, or 30 days before or after stem cells are introduced into the recipient. The short course of an immunosuppressive can be administered in conjunction with an anti-T cell antibody The short course of an immunosuppressive should be sufficient in concentration and duration to inactivate T cells, e.g., thymic or lymph node T cells, which would not be inactivated by antibody-based inactivation of T cells, e.g., inactivation by intravenous administrations of ATG antibody, or similar, preparations.

Other embodiments include (optionally): the step of, prior to hematopoietic stem cell transplantation, creating hematopoietic space, e.g., by irradiating the recipient mammal with low dose, e.g., less than 400, preferably less than 300, more preferably less than 200 or 100 rads, whole body irradiation to deplete or partially deplete the bone marrow of the recipient. As is discussed herein this treatment can be reduced or entirely eliminated.

Other preferred embodiments include: the step of, preferably prior to hematopoietic stem cell transplantation, depleting natural antibodies from the blood of the recipient mammal. Depletion can be achieved, by way of example, by contacting the recipients blood with an epitope which absorbs preformed anti-donor antibody. The epitope can be coupled to an insoluble substrate and provided, e.g., as an affinity column. E.g., $\alpha 1$–3 galactose linkage epitope-affinity matrix, e.g., matrix bound linear B type VI carbohydrate, can be used to deplete natural antibodies. Depletion can also be achieved by hemoperfusing an organ, e.g., a liver or a kidney, obtained from a mammal of the donor species. (In organ hemoperfusion antibodies in the blood bind to antigens on the cell surfaces of the organ and are thus removed from the blood.) Other preferred embodiments include those in which: the same mammal of the second species is the donor of one or both the graft and the hematopoietic cells; and the antibody is an anti-human thymocyte polyclonal anti-serum, obtained, e.g., from a horse or pig.

In preferred embodiments, the method includes the step of introducing into the recipient a graft obtained from the donor which is obtained from a different organ than the hematopoietic stem cells, e.g., a heart, pancreas, liver, or kidney.

Methods of the invention which substantially reduce or eliminate the need for hematopoietic space creating irradiation can be used when implanting allogeneic stem cells. Accordingly, in another aspect, the invention features a method of inducing tolerance in a recipient mammal of a first species to a graft from a donor mammal of the same species. The recipient mammal can be, by way of example, a primate, e.g., a human. The graft preferably expresses a major histocompatibility complex (MHC) antigen, preferably a class II antigen.

The method includes: introducing, e.g., by intravenous injection, into the recipient mammal, hematopoietic stem cells; and preferably, implanting the graft in the recipient. The hematopoietic cells are believed to prepare the recipient for the graft that follows, by inducing tolerance at both the B-cell and T-cell levels.

This method can be practiced without the administration of hematopoietic space-creating irradiation, e.g., whole body irradiation. Whole body irradiation is often used in the art to create hematopoietic space and thus promote engraftment, chimerism, and tolerance. The need for hematopoietic space-creating irradiation can be reduced or entirely eliminated by inclusion of one or more of the following steps in the method:

(1) Administering a sufficiently large number of donor hematopoietic cells to the recipient such that donor stem cells engraft, give rise to mixed chimerism, and induce tolerance, preferably, the stem cells are administered in combination with one or more of the treatments disclosed herein, e.g., (2) or (3) immediately below;

(2) Administering hematopoietic space creating antibodies or drugs to the recipient. E.g., administering an inhibitor of cell proliferation, e.g., DSG, or an anti-metabolite, e.g. brequinar, or an anti-T cell antibody, e.g., one or both of an anti-CD4 or anti-CD8 antibody.

(3) creating thymic space in the recipient, e.g., by irradiating the thymus of the recipient, e.g., by administering between 100 and 1,000, more preferably between 300 and 700, e.g., 700 rads, of thymic irradiation, or by administering anti-T cell antibodies in sufficient dose to inactivate thymocytes. Other methods for the creation of thymic space include: the administration of steroids, corticosteroids, brequinar or an immune suppressant chemical or drug, e.g, rapamycin, cyclosporin, or FK506. Treatment to create thymic space should be administered, or at least begun, prior to the administration of hematopoietic stem cells. An effective treatment should deplete single positive thymocytes to an extent that engraftment and the formation of mixed chimerism is optimized in the absence of the creation of hematopoietic space, e.g., hematopoietic space created by whole body irradiation. In preferred embodiments the subject's single positive thymocytes are depleted by at least 20, 40, 60, or 80%. Treatments which result in between 10 and 90% depletion are preferred. The length of the treatment will vary with dosage and the effectiveness of the agent but will generally be less than 60, 30, or 15 days. The treatment should last at least 7, and more preferably 10, or 14 days in length. In preferred courses of treatment, e.g., the administration of an immunosuppressive chemical or drug, e.g., cyclosporine, should last between 7 and 30 days. The treatment, e.g., the administration of cyclosporin, should be started at a time such that it is completed prior to the administration of stem cells. Administration of the agent should be on a daily basis or as needed to maintain a level of the agent which allows the desired level of depletion. A particularly preferred treatment is the administration of an immunosuppresive chemical, e.g., cyclosporin, for more than 7 and less than 30 days. A useful regimen in rodents is 20 mg/kg/day cyclosporin for 14 days ending on the third day before administration of stem cells.

Thus, in preferred embodiments a quantity of hematopoietic stem cells sufficient to induce tolerance, without the need for hematopoietic space-creating irradiation, is administered to the recipient. In preferred embodiments the number of donor hematopoietic cells is at least twice, is at least equal to, or is at least 75, 50, or 25% as great as, the number of bone marrow cells found in an adult of the recipient species. In preferred embodiments the number of donor hematopoietic stem cells is at least twice, is at least equal to, or is at least 75, 50, or 25% as great as, the number of bone marrow hematopoietic stem cells found in an adult of the recipient species.

In preferred embodiments, mixed chimerism is induced in the recipient and the state of mixed chimerism is formed in the absence of the induction of hematopoietic space, e.g., in the absence of hematopoietic space created by space creating irradiation, e.g., whole body irradiation.

The number of donor cells administered to the recipient can be increased by either or both of increasing the number of stem cells provided in a particular administration or by providing repeated administrations of donor stem cells.

Repeated stem cell administration can promote engraftment, mixed chimerism, and long-term deletional tolerance in graft recipients. Thus, the invention also includes methods in which multiple hematopoietic stem cells administrations are provided to a recipient. Multiple administration can substantially reduce or eliminate the need for hematopoietic space-creating irradiation. Administrations can be given prior to, at the time of, or after graft implantation. In preferred embodiments multiple administrations of stem cells are provided prior to the implantation of a graft. Two, three, four, five, or more administrations can be provided. The period between administrations of hematopoietic stem cells can be varied. In preferred embodiments a subsequent administration of hematopoietic stem cell is provided: at least two days, one week, one month, or six months after the previous administration of stem cells; when the recipient begins to show signs of host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain a level of mixed chimerism sufficient to maintain tolerance to donor antigen.

One or more post graft-implantation-administrations of donor stem cells can also be provided to minimize or eliminate the need for irradiation. Post graft administration of hematopoietic stem cell can provided: at least two days, one week, one month, or six months after the previous administration of stem cells; at least two days, one week, one month, six months, or at any time in the life span of the recipient after the implantation of the graft; when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain tolerance or otherwise prolong the acceptance of a graft.

When multiple stem cell administrations are given one or more of the administrations can: include a number of donor hematopoietic cells which is at least twice, is equal to, or is at least 75, 50, or 25% as great as, the number of bone marrow cells found in an adult of the recipient species; include a number of donor hematopoietic stem cells which is at least twice, is equal to, or is at least 75, 50, or 25% as great as, the number of bone marrow hematopoietic stem cells found in an adult of the recipient species.

In preferred embodiments the method includes inactivating natural killer cells, preferably graft reactive or donor reactive NK cells, of the recipient mammal. This can be accomplished, e.g., by introducing into the recipient mammal an antibody capable of binding to natural killer cells of the recipient mammal. The administration of antibodies, or other treatment to inactivate natural killer cells, can be given prior to introducing the hematopoietic stem cells into the recipient mammal or prior to implanting the graft in the recipient. This antibody can be the same or different from an antibody used to inactivate T cells.

In preferred embodiments the method includes inactivating T cells, preferably graft reactive or donor reactive T cells, of the recipient mammal. This can be accomplished, e.g., by introducing into the recipient mammal an antibody capable of binding to T cells of the recipient mammal. The administration of antibodies, or other treatment to inactivate T cells, can be given prior to introducing the hematopoietic stem cells into the recipient mammal or prior to implanting the graft in the recipient. This antibody can be the same or different from an antibody used to inactivate natural killer cells One source of anti-NK antibody is anti-human thymocyte polyclonal anti-serum. Preferably, a second anti-mature T cell antibody can be administered as well, which lyses T cells as well as NK cells. Lysing T cells is advantageous for both bone marrow and graft survival. Anti-T cell antibodies are present, along with anti-NK antibodies, in anti-thymocyte anti-serum. Repeated doses of antibodies, e.g., anti-NK or anti-T cell antibodies, may be preferable. Monoclonal preparations can be used in the methods of the invention.

In preferred embodiments the recipient does not receive treatments which stimulate the release of a cytokine by mature T cells. E.g., the recipient should not receive a substance, e.g., a steroid drug, e.g., Prednisone (17,21-dihydroxypregna-1,4-diene-3,11,20-trione), at a dosage or concentration which stimulates the release of a cytokine by mature T cells in the recipient. Preferably, the recipient is free of such treatment from the time stem cells are first administered until the graft is implanted or until mixed chimerism and tolerance is established.

In preferred embodiments the method includes the administration of a short course of help reducing treatment, e.g., a drug or other chemical, which induces tolerance to unmatched class I and/or minor antigens on the graft which is introduced into the recipient. The short course of help reducing treatment, e.g., a short course of high dose cyclosporine, is generally administered at the time at the graft is introduced into the recipient. The duration of the short course of help reducing treatment is approximately equal to or is less than the period required for mature T cells of the recipient species to initiate rejection of an antigen after first being stimulated by the antigen; in more preferred embodiments, the duration is approximately equal to or is less than two, three, four, five, or ten times, the period required for a mature T cell of the recipient species to initiate rejection of an antigen after first being stimulated by the antigen. These methods are described in more detail in co-owned application Ser. No. 08/458,720, filed Jun. 1, 1995, which is hereby incorporated by references. Methods of Ser. No. 08/458,720 can be combined with the methods described herein.

Other preferred embodiments include treatments to further inactivate recipient T cells, particularly thymic or lymph node thymocytes or T cells. Thymic or lymph node thymocytes or T cells might otherwise inhibit the engraftment or survival of the administered cells. Such inactivation can be accomplished by one or more of: irradiating the thymus of the recipient mammal with a dose of radiation sufficient to inactivate thymocytes, e.g., 100–1,000, more preferably between 300 and 700, e.g., about 350 or 700 rads of thymic irradiation; administering one or repeated doses of an anti-T cell or anti-thymocyte antibody; or administering to the recipient a short course of an immunosuppressant chemical or drug, as is described herein. Inactivation of thymocytes or T cells can be performed prior to hematopoietic stem cell or graft transplantation. In preferred embodiments the method includes diminishing or inhibiting thymocyte or T cell activity, preferably the activity of thymic or lymph node T cells by administering to the recipient a short course of an immunosuppressive agent, e.g., cyclosporine, sufficient to inactivate thymocytes or T cells, preferably thymic or lymph node T cells. The duration of the short course of immunosuppressive agent is: approximately equal to 30 days; approximately equal to or less than 8–12 days, preferably about 10 days; approximately equal to or less than two, three, four, five, or ten times the 8–12 or 10 day period. The short course can begin: before or at about the time the treatment to induce tolerance is begun, e.g., at about the time stem cells are introduced into the recipient; on the day the treatment to induce tolerance is begun, e.g., on the day stem cells are introduced into the recipient; within 1, 2, 4, 6, 8, 10, or 30 days before or after the treatment to induce tolerance is begun, e.g., within 1, 2, 4, 6, 8, 10, or 30 days before or after stem cells are introduced into the recipient. The short course of an immunosuppressive can be administered in conjunction with an anti-T cell antibody. The short course of an immunosuppressive should be sufficient in concentration and duration to inactivate T cells, e.g., thymic or lymph node T cells, which would not be inactivated by antibody-based inactivation of T cells, e.g., inactivation by intravenous administrations of ATG antibody, or similar, preparations.

Other embodiments include (optionally): the step of, prior to hematopoietic stem cell transplantation, creating hematopoietic space, e.g., by irradiating the recipient mammal with low dose, e.g., less than 400, preferably less than 300, more preferably less than 200 or 100 rads, whole body irradiation to deplete or partially deplete the bone marrow of the recipient. As is discussed herein this treatment can be reduced or entirely eliminated.

In another aspect, the invention features a method of inducing tolerance to, or prolonging acceptance of, a graft from a donor mammal. The method includes: diminishing or inhibiting thymocyte or T cell activity, preferably the activity of thymic or lymph node T cells, by administering to the recipient, a short course of an immunosuppressive agent, e.g., a drug or other chemical, e.g., cyclosporine, sufficient to inactivate thymocytes or T cells, preferably thymic or lymph node T cells. The duration of the short course of immunosuppressive agent is: approximately equal to 30 days; approximately equal to or less than 8–12 days, preferably about 10 days; approximately equal to or less than two, three, four, five, or ten times the 8–12 or 10 day period. The short course can begin: before the introduction of door tissue into the recipient, preferably and will end 1, 2, 4, 6, 8, 10, or 30 days before introduction of donor tissue.

In preferred embodiments: the recipient is a primate, e.g., a human, and the graft is an allograft; the recipient is a primate, e.g., a human, and the donor is from a second species, e.g., a second primate species or a swine.

This method can be combined with any of the other methods described herein.

"Discordant species combination", as used herein, refers to two species in which hyperacute rejection occurs when a graft is grafted from one to the other. Generally, discordant species are from different orders, while non-discordant species are from the same order. For example, rats and mice are non-discordant concordant species. Concordant species combinations do not exhibit hyperacute rejection.

"Graft", as used herein, refers to a body part, organ, tissue, or cells. Organs such as liver, kidney, heart or lung, or other body parts, such as bone or skeletal matrix, tissue, such as skin, intestines, endocrine glands, or progenitor stem cells of various types, are all examples of grafts.

"Help reducing agent", as used herein, is an agent, e.g., an immunosuppressive drug, which results in the reduction of cytokine release. Examples of help reducing agents are cyclosporine, FK-506, and rapamycin. Anti-T cell antibodies, because they can eliminate T cells, are not preferred for use as help reducing agents. A help reducing agent must be administered in sufficient dose to give the level of inhibition of cytokine release which will result in tolerance. The help reducing agent should be administered in the absence of treatments which promote cytokine, e.g., IL-2, release. Putative help reducing agents can be prescreened by in vitro or in vivo tests, e.g., by contacting the putative agent with T cells and determining the ability of the treated T cells to release a cytokine, e.g., IL-2. The inhibition of cytokine release is indicative of the putative agent's efficacy as a help reducing agent. Such prescreened putative agents can then be further tested in a kidney transplant assay. In a kidney transplant assay a putative help reducing agent is tested for efficacy by administering the putative agent to a recipient monkey and then implanting a kidney from a class II matched class I and minor antigen mismatched donor monkey into the recipient. Tolerance to the donor kidney (as indicated by prolonged acceptance of the graft) is indicative that the putative agent is, at the dosage tested, a help reducing agent.

"Help reduction", as used herein, means the reduction of T cell help by the inhibition of the release of at least one cytokine, e.g., any of IL-2, IL-4, IL-6, gamma interferon, or TNF, from T cells of the recipient at the time of the first exposure to an antigen to which tolerance is desired. The inhibition induced in a recipient's T cell secretion of a cytokine must be sufficient such that the recipient is tolerized to an antigen which is administered during the reduction of help. Although not being bound by theory, it is believed that the level of reduction is one which substantially eliminates the initial burst of IL-2 which accompanies the first recognition of a foreign antigen but which does not eliminate all mature T cells, which cells may be important in educating and producing tolerance.

"Hematopoietic space", as used herein, refers to a condition created in the bone marrow which promotes engraftment of administered stem cells. The most common way of creating hematopoietic space is by irradiation of the bone marrow with whole body irradiation.

"Hematopoietic stem cell", as used herein, refers to a cell, e.g., a bone marrow cell, or a fetal liver or spleen cell, which is capable of developing into all myeloid and lymphoid lineages and by virtue of being able to self-renew can provide long term hematopoietic reconstitution. Purified preparations of hematopoietic cells or preparations, such as bone marrow, which include other cell types, can be used in methods of the invention. Although not wishing to be bound by theory, it is believed that the hematopoietic stem cells home to a site in the recipient mammal. The preparation should include immature cells, i.e., undifferentiated hematopoietic stem cells; these desired cells can be separated out of a preparation or a complex preparation can be administered. E.g., in the case of bone marrow stem cells, the desired primitive cells can be separated out of a preparation or a complex bone marrow sample including such cells can be used. Hematopoietic stem cells can be from fetal, neonatal, immature or mature animals. Stem cells derived from the cord blood of the recipient or the donor can be used in methods of the invention. See U.S. Pat. No. 5,192,553, hereby incorporated by reference, and U.S. Pat. No. 5,004, 681, hereby incorporated by reference.

"Immunosuppressive agent capable of inactivating thymic or lymph node T cells", as used herein, is an agent, e.g., a chemical agent, e.g., a drug, which, when administered at an appropriate dosage, results in the inactivation of thymic or lymph node T cells. Examples of such agents are cyclosporine, FK-506, and rapamycin. Anti-T cell antibodies can also be used. An agent should be administered in sufficient dose to result in significant inactivation of thymic or lymph node T cells which are not inactivated by administration of an anti-T cell antibody, e.g., an anti-ATG preparation. Putative agents, and useful concentrations thereof, can be prescreened by in vitro or in vivo tests, e.g., by administering the putative agent to a test animal, removing a sample of thymus or lymph node tissue, and testing for the presence of active T cells in an in vitro or in vivo assay. Such prescreened putative agents can then be further tested in transplant assays.

"Thymic or lymph node or thymocytes or T cell", as used herein, refers to thymocytes or T cells which are resistant to inactivation by traditional methods of T cell inactivation, e.g., inactivation by a single intravenous administration of anti-T cell antibodies, e.g., anti-bodies, e.g., ATG preparation.

"Thymic irradiation", as used herein, refers to a treatment in which at least half, and preferably at least 75, 90, or 95% of the administered irradiation is targeted to the thymus. Whole body irradiation, even if the thymus is irradiated in the process of delivering the whole body irradiation, is not considered thymic irradiation.

"MHC antigen", as used herein, refers to a protein product of one or more MHC genes; the term includes fragments or analogs of products of MHC genes which can evoke an immune response in a recipient organism. Examples of MHC antigens include the products (and fragments or analogs thereof) of the human MHC genes, i.e., the HLA genes. MHC antigens in swine, e.g., miniature swine, include the products (and fragments and analogs thereof of the SLA genes, e.g., the DRB gene.

"Miniature swine", as used herein, refers to a wholly or partially inbred pig.

"Hematopoietic space-creating irradiation", as used herein, refers to irradiation directed to the hematopoietic tissue, i.e., to tissue in which stem cells are found, e.g., the bone marrow. It is of sufficient intensity to kill or inactivate a substantial number of hematopoietic cells. It is often given as whole body irradiation.

"Thymic space" as used herein, is a state created by a treatment that facilitates the migration to and/or development in the thymus of donor hematopoietic cells of a type which can delete or inactivate host thymocytes that recognize donor antigens. It is believed that the effect is mediated by elimination of host cells in the thymus.

"Short course of a help reducing agent", as used herein, means a transitory non-chronic course of treatment. The treatment should begin before or at about the time of transplantation of the graft. Alternatively, the treatment can begin before or at about the time of the recipient's first exposure to donor antigens. Optimally, the treatment lasts for a time which is approximately equal to or less than the period required for mature T cells of the recipient species to initiate rejection of an antigen after first being stimulated by the antigen. The duration of the treatment can be extended to a time approximately equal to or less than two, three, four, five, or ten times, the period required for a mature T cell of the recipient species to initiate rejection of an antigen after first being stimulated by the antigen. The duration will usually be at least equal to the time required for mature T cells of the recipient species to initiate rejection of an antigen after first being stimulated by the antigen. In pigs and monkeys, about 12 days of treatment is sufficient. Experiments with cyclosporine A (10 mg/kg) in pigs show that 6 days is not sufficient. Other experiments in monkeys show that IL-2 administered on day 8, 9, or 10 of cyclosporine A treatment will result in rejection of the transplanted tissue. Thus, 8, 9, or 10 days is probably not sufficient in pigs. In monkeys, a dose of 10 mg/kg cyclosporine with a blood level of about 500–1,000 ng/ml is sufficient to induce tolerance to class II matched class I and minor antigen mismatched kidneys. The same blood level, 500–1,000 ng/ml, is sufficient to induce tolerance in pigs. Long-term administration of 5 mg/kg prevents rejection (by long term immune suppression) but does not result in tolerance.

"Short course of a immunosuppressive agent", as used herein, means a transitory non-chronic course of treatment. The treatment should begin before or at about the time the treatment to induce tolerance is begun, e.g., at about the time, xenogeneic, allogeneic, genetically engineered syngeneic, or genetically engineered autologous stem cells are introduced into the recipient. e.g., the short course can begin on the day the treatment to induce tolerance is begun, e.g., on the day, xenogeneic, allogeneic, genetically engineered syngeneic, or genetically engineered autologous stem cells are introduced into the recipient or the short course can begin within 1, 2, 4, 6, 8, or 10 days before or after the treatment to induce tolerance is begun, e.g., within 1, 2, 4, 6, 8, or 10 days before or after xenogeneic, allogeneic, genetically engineered syngeneic, or genetically engineered autologous stem cells are introduced into the recipient. The short course can last for: a period equal to or less than about 8–12 days, preferably about 10 days, or a time which is approximately equal to or is less than two, three, four, five, or ten times the 8–12 or 10 day period. Optimally, the short course lasts about 30 days. The dosage should be sufficient to maintain a blood level sufficient to inactivate thymic or lymph node T cells. A dosage of approximately 15 mg/kg/day has been found to be effective in primates.

"Stromal tissue", as used herein, refers to the supporting tissue or matrix of an organ, as distinguished from its functional elements or parenchyma.

"Tolerance", as used herein, refers to an inhibition of a graft recipient's immune response which would otherwise occur, e.g., in response to the introduction of a nonself MHC antigen into the recipient. Tolerance can involve humoral, cellular, or both humoral and cellular responses. Tolerance, as used herein, refers not only to complete immunologic tolerance to an antigen, but to partial immunologic tolerance, i.e., a degree of tolerance to an antigen which is greater than what would be seen if a method of the invention were not employed. Tolerance, as used herein, refers to a donor antigen-specific inhibition of the immune system as opposed to the broad spectrum inhibition of the immune system seen with immunosuppressants.

Methods of the invention minimize or eliminate the need for hematopoietic space-creating treatment, e.g., irradiation, in many methods of tolerance induction.

In methods of the invention, the creation of thymic space, e.g., by thymic irradiation, the inactivation of recipient peripheral T cells and thymocytes, and the administration of a sufficiently large number of xenogeneic or allogeneic donor stem cells allows the induction of tolerance without subjection the recipient to WBI. The induction of thymic space can reduce the level of donor reactive thymocytes but additional steps (described herein) can be added to further diminish donor thymocyte reactivity.

Other features and advantages of the invention will be apparent from the following detailed description, and from the claims.

DETAILED DESCRIPTION

The drawings will first be briefly described.
Drawings

Figure 1:
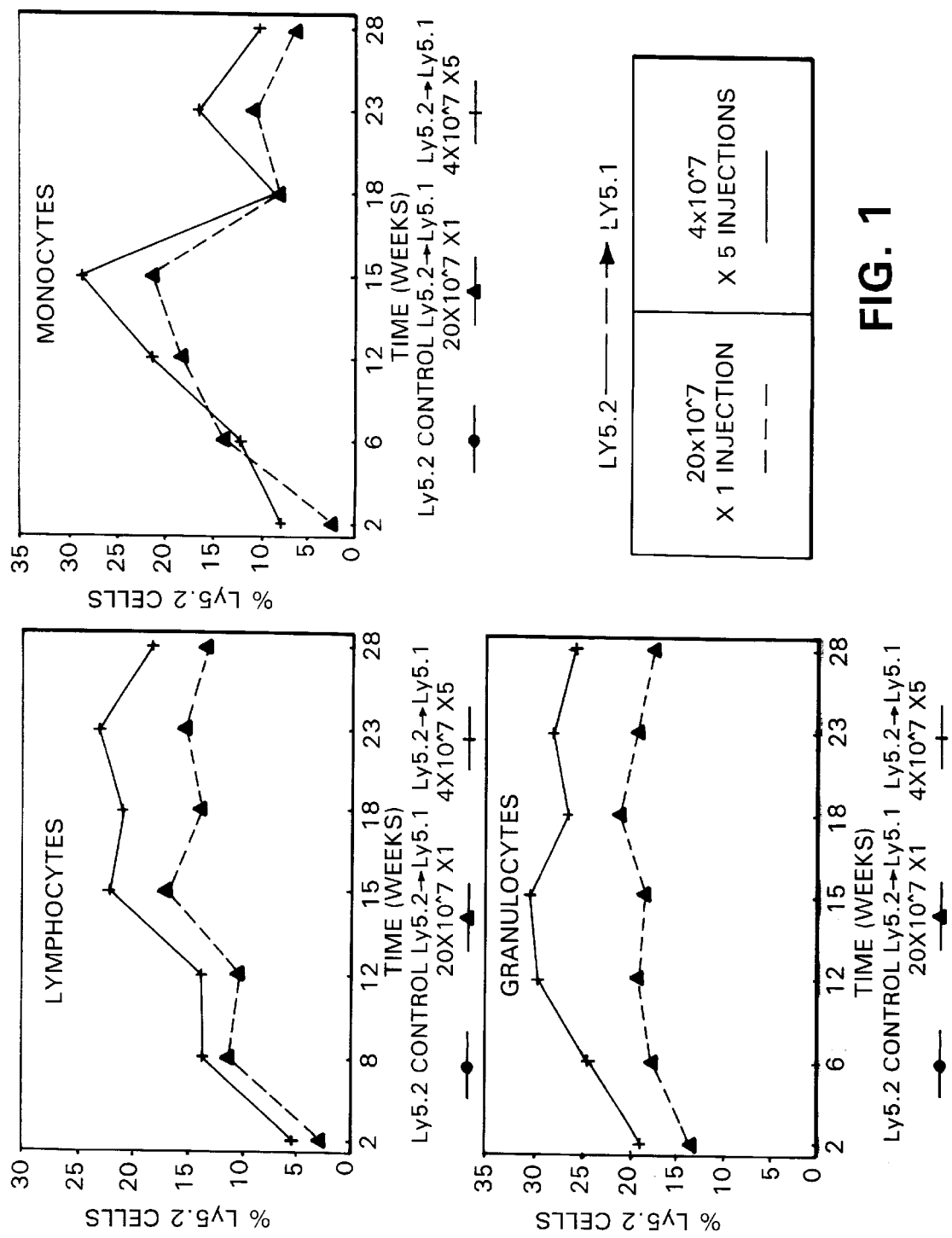

FIG. 1 is a depiction of multilineage analysis of donor repopulation in animals administered either one injection (----) or five injections (____) of BMC.

Figure 2:
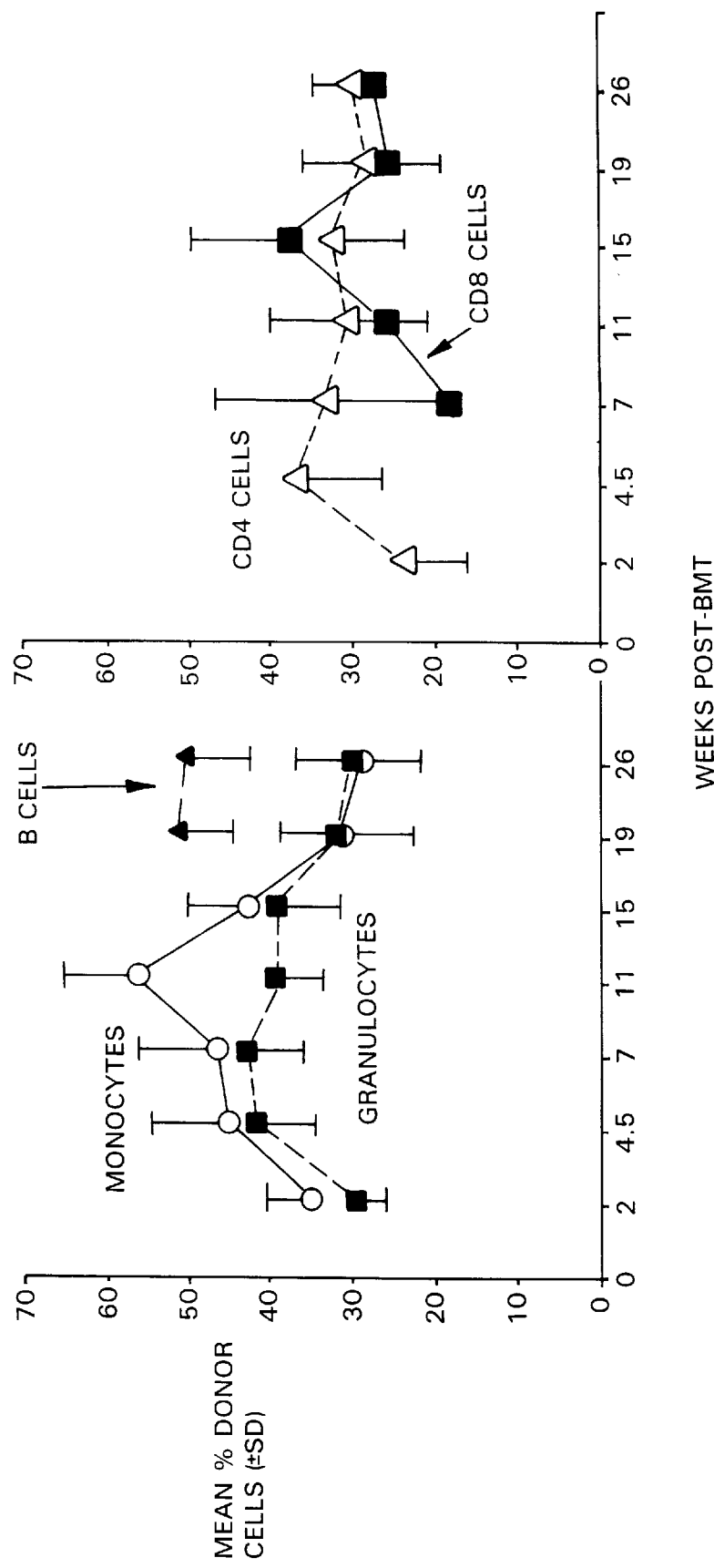

FIG. 2 (left panel) is a graph of long-term donor monocyte (○), granulocyte (■), and B cell (solid triangle) repopulation in WBC of stable chimeras among B6 mice receiving anti-CD4 and CD8 mAbs on days −5, −1 and 7, 6 Gy TI on day 0, with $174 \times 10^6$ B10.A BMC over five days, from day 0 through 4 (n=7). Standard deviations are shown on each data point. The right panel shows that Mean ±SD percentages of total CD4 (△) and CD8 (■) cells of donor origin in WBC of the same mice shown in the left panel.

Figure 3:
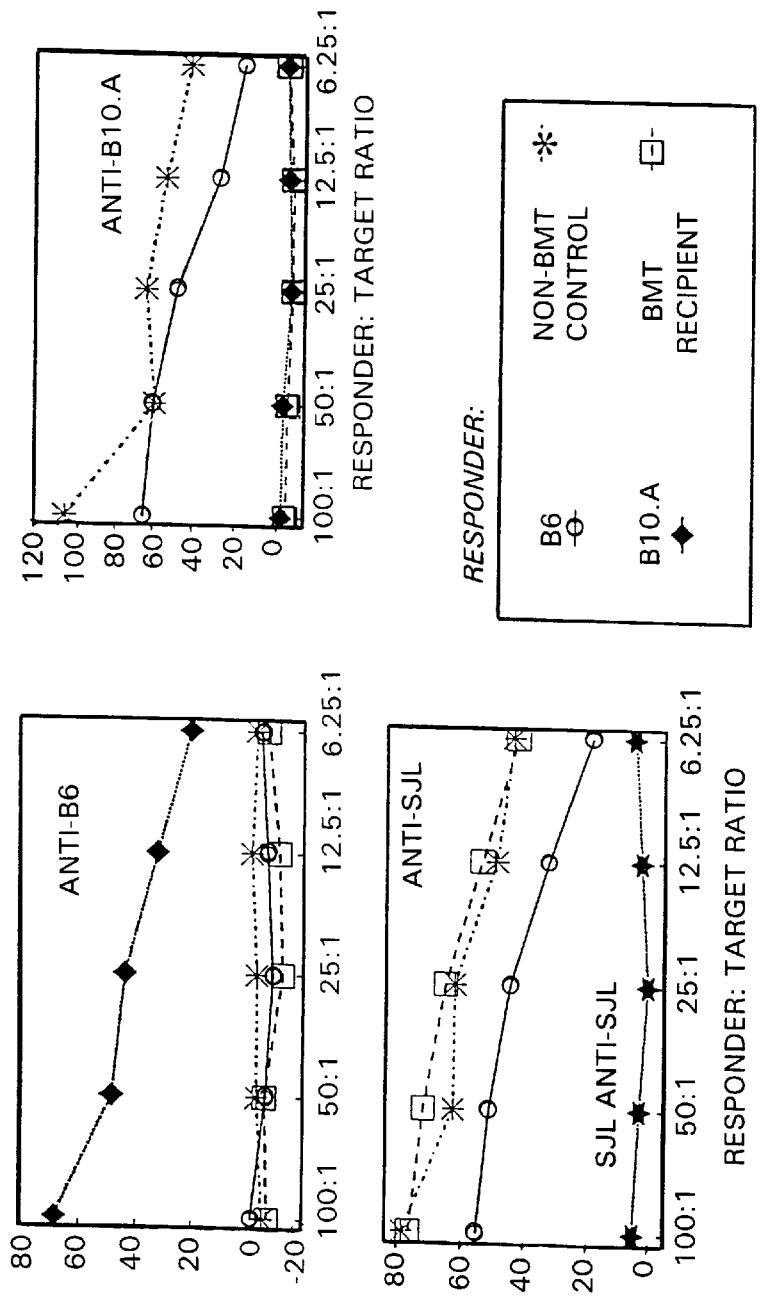

FIG. 3 is a depiction of CML responses of spleen cells from stable mixed chimeras. B6 mice treated with anti-CD4 and CD8 mAbs on days −5, −1 and 7, TI on day 0, and high-dose B10.A BMC($174 \times 10^6$ cells over days 0 through 4) were analyzed 25 to 29 weeks post-BMT. CML reactivity to host-type (top left panel), donor-type (top right panel), and third party (bottom panel) stimulators and targets is shown for: (□) a mixed chimera; (*) a non-BMT control/(○) a normal B6 mouse and; (◆) a normal B10.A mouse. Percent specific lysis was calculated using the following formula: 100%×(Experimental $^{51}$Cr release−Spontaneous $^{51}$Cr release)/(Maximum $^{51}$Cr release−Spontaneous $^{51}$Cr release). The chart at the bottom of the figure shows maximum % specific lysis obtained for three additional chimeras.

Figure 4:
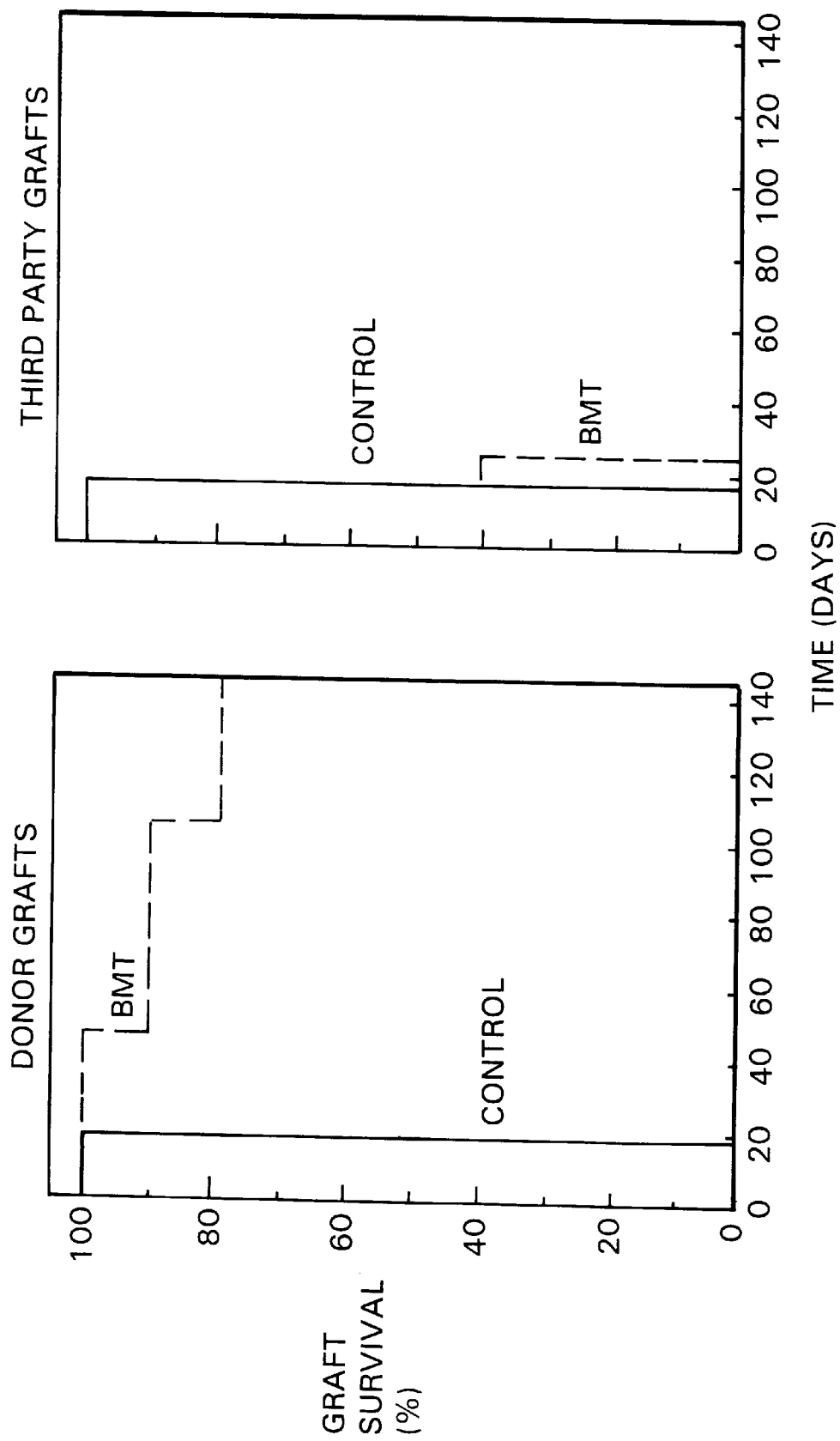

FIG. 4 is a graph showing the specific acceptance of donor-specific skin grafts in B6 recipients of allogeneic B10.A BMT ($174 \times 10^6$ days 0 through 4) after treatment with anti-CD4 and CD8 mAbs on days −5, −1 and 7, with 7 Gy of TI on day 0. Left panel: Survival of donor-type skin on similarly-treated non-BMT control mice (____) and BMT recipients (---). Right panel: Survival of third party (SJL/J) skin on the same groups of mice. Grafting was performed seven weeks post-BMT.

Figure 5:
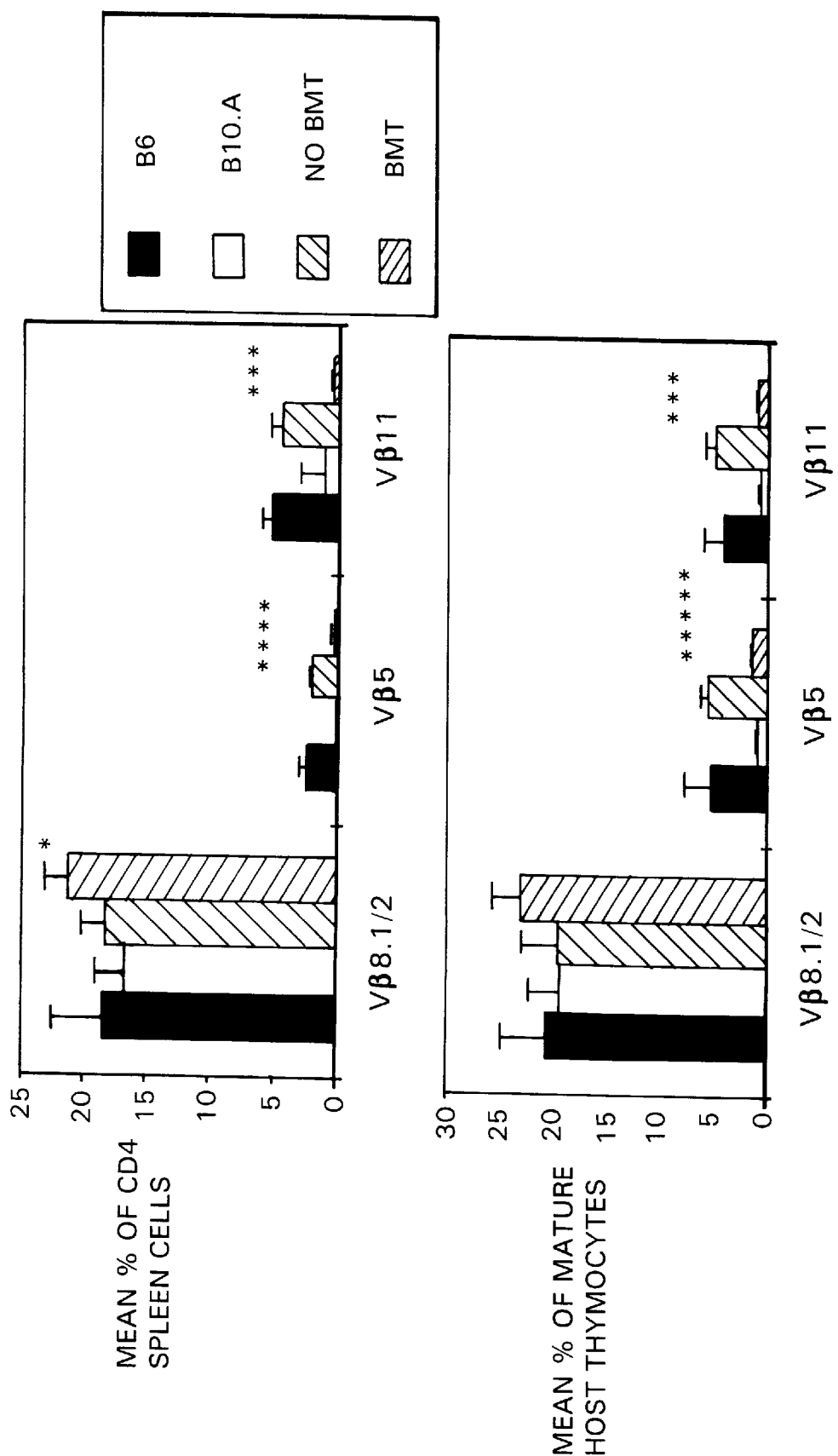

FIG. 5 is a depiction of the specific deletion of Vβ5+ and Vβ11+ cells among CD4+ spleen cells and among mature (class I$^{high}$) host-type (K$^{bhigh}$) thymocytes of chimeras sacrificed 24 to 29 weeks post BMT. For b10.A control mice, gated H-2D$^{bhigh}$ thymocytes were analyzed instead. B6 mice received $174 \times 10^6$ B10.A BMC over days 0–4 after conditioning with anti-CD4 and -CD8 mAbs and 7 Gy TI. FCM analysis was performed on $10^4$ gated cells for each population of interest. The total number of TCRαβ$^{high}$ cells in the same gate was also determined, and the results obtained for each individual Vβ were corrected by dividing by the fraction of TCRαβ$^{high}$ cells. Results are presented for stable chimeras (n=6). *denotes P<0.05; *, P<0.005; , P<0.0005; ***, P<0.00005 compared to simultaneous, similarly-treated non-BMT controls (n=4).

Overview

The invention provides several methods of inducing tolerance to foreign antigens, e.g., to antigens on allogeneic or xenogeneic tissue or organ grafts. These methods can be used individually or in combination.

Section I below presents animal trials in which it is shown that engraftment, mixed chimerism, and tolerance can be induced without the need for hematopoietic space-creating irradiation.

Section II below describes sources of cells for transplantation.

Section III below discusses implantation of bone marrow cells to induce tolerance to MHC disparity.

EXAMPLE 1

I. The Effect of Thymic Irradiation on Syngeneic Engraftment Using High Doses of Donor Bone Marrow Animals. Female C57BL/6NCR (B6; H-2b. Ly-5.2) and female Ly-5 congenic B6.Ly-5.2 (Ly-5.1) mice were obtained from the Frederick Cancer Research Facility (Frederick, Md.). Ly-5 alleles are described according to the nomenclature of Morse et al. (1987. Immunogenetics 25:71). All mice were housed in sterilized microisolator cages in which they received autoclaved food and autoclaved acidified drinking water. Recipients were age-matched and were used at 12 to 16 weeks of age.

BMT. C57BL/6NCR (B6; H-2b. Ly-5.2) mice received 100 ml each of ascites containing anti-CD4 mAb GK1.5 and anti-CD8 mAb 2.43 intraperitoneally on days −6 and −1 and +7. This volume of ascites contained 1–2 mg of GK1.5 and 1.25–1.5 mg of 2.43 respectively, as measured by rat IgG2b-specific ELISA. Animals were irradiated with either 0, 3.5 or 7 Gy thymic irradiation on day 0. One series of mice was treated with one dose of 200 million bone marrow cells (BMC). A second series of mice were treated, starting on day 0 and repeated daily for a total of five days, with forty million (total 200 million cells)BMC from Ly-5 congenic B6.Ly-5.2 (Ly-5.1) mice were administered intravenously. BM cells (BMCs, $200 \times 10^6$) were obtained from the tibiae and femora of sexmatched B6, Ly-5.2 donors aged 6 to 14 weeks. T cell depletion was performed as described in Sykes et al. (1990. PNAS, 87: 5633–5637) using anti-CD4 and CD8 mAbs and rabbit complement.

Cell counts. Heparinized peripheral blood was analyzed on an Automated Cell Counter (System 9000; Serono-Baker Diagnostics Inc. Allentown, Pa.).

Phenotyping. Phenotyping was performed at various times beginning 2 weeks after BMT. Animals were tail bled and white blood cells (WBCs) were prepared by hypotonic shock. Suspensions of spleen cells, thymocytes. BMCs, and BM colonies were also analyzed. Staining with both donor-specific and recipient-specific mAB was performed on each chimera and control animal. Cells were incubated with 20 mL undiluted culture supernatant of A20-1.7 (anti-Ly-5.1 mAb; mouse IgG2a) or 104-2.1 (anti-Ly-5.2 mAB; mouse IgG2a) (hybridomas kindly provided by Dr. S. Kimura, Sloan Kettering Cancer Institute. New York, N.Y.) for 30 minutes at 4° C. and then washed twice. To block nonspecific FcgR binding of labeled antibodies, 10 mL undiluted culture supernatant of 2.4G2 (rat antimouse FcgR mAb) was added to the first incubation. Cell-bound mAbs were detected with fluorescein isothiocyanate (FITC)-conjugated rat antimouse IgG2a mAb (Zymed laboratories. Inc. Mundelein, Ill.), which was incubated for 30 minutes at 4° C. followed by two washes and analysis on an FACScan (Becton Dickinson, Mountain View, Calif.). In all experiments, the percentage of cells staining with each mAb was determined from one-color fluorescence histograms and comparison with those obtained from normal donor and host-type animals, which were used as positive and negative controls. The percentage of cells considered positive after staining with an mAb was determined using a cutoff chosen as the fluorescence level at the beginning of the positive peak for the positive control strain, and by subtracting the percentage of cells stained with an irrelevant mAb (nonreactive IgG2a mAb HOPC 1 plus FITC-conjugated antimouse IgG2a mAb). The relative percent staining of a chimera with mAb was calculated using the formula: 100%× (net chimera percent positive)–(net negative control percent positive)/(net positive control percent positive)–(net negative control percent positive), in which net percent positive refers to the percentage obtained after subtraction of staining with HOPC 1, and positive and negative controls were cells from appropriate normal Ly-5.1+ and Ly-5.2+ mice. For test cell populations in which staining with an anti-Ly-5 mAb was less than that of the negative control and the calculated percent chimerism was therefore less than 0, the values are reported as 0. Using this method of calculation, less than 0.1% contaminating Ly-5.1+ cells could be detected in artificial Ly-5.2 (99.9%)/Ly-5.1 (0.1%) mixtures. However, a visible positive peak was not detectable in artificial mixtures containing 0. 1; or fewer Ly-5.1+ cells, but was visible with 1% contaminating Ly-5.1+ cells (data not shown). All hematopoietic lineages stained strongly with anti-Ly-5 mAb. By using forward and 90° light scatter (FSC and SSC respectively) dot plots lymphocyte (FSC- and SSC-low population), granulocyte (SSC-high population) and monocyte (FSC-high but SSC-low population) populations were gated, and chimerism was determined separately for each population. All SSC-high cells in the granulocyte gate stained with FITC-conjugated antimouse granulocyte mAb (Gr-l). Dead cells were excluded by gating out low FSC/high propidium iodide-retaining cells.

Engraftment without thymic irradiation. Two groups of animals were administered either one injection of 20×10$^7$ BMC or five injections on a daily basis of 40×10$^6$ BMC. Multilineage analysis of donor repopulation showed that all lineages showed 10–25% long-term chimerism which remained stable for at least 30 weeks (FIG. 1). Thus, when multiple high doses of bone marrow cells are injected into the recipient mouse stable engraftment of hematopoietic stem cells can occur.

Engraftment with thymic irradiation. Significantly high levels of engraftment were observed in the CD4 T cell population when the mice were pretreated with thymic irradiation Table 1, increasing from approximately 0–10% to between 20–60%. Repopulation of the monocyte lineage was increased from a level of approximately 20% to between 30 to 40%. This is in agreement with the results previously shown that 3.5 Gy WBI is sufficient to enable stable engraftment in the syngeneic setting. These results indicate that while engraftment can be achieved in the absence of either WBI or TI a relatively low dose of thymic irradiation (3.5 Gy) enables a higher level of syngeneic engraftment to be obtained.

TABLE 1

The effect of Thymic Irradiation on Syngeneic Engraftment

| Thymic Irradiation | % Engrafiment at Day 30 | |
|---|---|---|
| | CD4+ | Monocytes |
| 0 | ND* | 20.8 |
| | 11.5 | 18.2 |
| | ND | 25.3 |
| | ND | 19.4 |
| 3.5 Gy | 31.0 | 31.4 |
| | 36.6 | 31.5 |
| | 64.3 | 28.8 |
| | 28.4 | 29.6 |
| 7.0 Gy | 37.0 | 39.0 |
| | 71.3 | 36.7 |
| | 41.2 | 41.5 |

*Not detectable

EXAMPLE 2

Induction of High Levels of Allogeneic Hematopoietic Reconstitution and Donor-Specific Tolerance Without Myelosuppressive Conditioning Pluripotent hematopoietic stem cells (PHSC) engraft in unconditioned recipients given high doses of syngeneic or Ly5 congenic marrow. Allogeneic PHSC engraftment was achieved by administering a high dose (200×10$^6$) of fully MHC-mismatched B10.A (H-2$^a$) BMC to B6 (H-2$^b$) recipients. The recipients were conditioned only with depleting anti-CD4 and anti-CD8 mAbs on days −5, −1 and 7. Initial chimerism was achieved among peripheral blood lymphocytes, monocytes and granulocytes, with peak levels of 15–33% donor cells at four to six weeks post-BMT. However, initial T cell chimerism was low (<10%), and multilineage chimerism tended to decline with time. Table 2 shows the low levels of chimerism in spleen, marrow and thymus of animals sacrificed 12 to 25 weeks after BTM.

In order to optimize engraftment thymic space was induced by the administration of thymic irradiation (TI). B6 mice received anti-T cell mAbs as above, 7 Gy TI on day 0, and a total of 174×10$^6$ fully MHC-mismatched B10.A BMC on days 0 through 4. In seven of ten animals, donor cells constituted a high proportion of WBC monocytes, granulocytes, B cells and CD4 and CD8 cells at all times (FIG. 2). In seven animals, the level of initial donor CD4 T cell was similar to that of other lineages, and chimerism in all lineages was stable throughout the six-month follow-up period (FIG. 2). However, in three animals, despite initially high levels of chimerism, donor representation declined in some or all lineages over time (data not shown).

Recipients of the TI-containing high-dose allogeneic BMT regimen were sacrificed 24 to 29 weeks following BMT, and chimerism was evaluated in other tissues. Most stable WBC chimeras showed substantial chimerism among BMC, splenic B and T cells, and class I$^{high}$, mature thymocytes (Table 2). These thymi also contained donor class I$^{low}$, immature thymocytes. Unlike stable chimeras, thymi from the three "unstable" chimeras (Table 2) contained few donor-derived class I$^{high}$ cells, and showed variable splenic T and B cell and BMC chimerism (Table 2).

The stable, high-level, multilineage chimerism observed in most mice demonstrates that substantial allogenic PHSC engraftment can be achieved without WBI in mice receiving T cell-depleting mAbs, 7 Gy TI, and high-dose allogeneic marrow. Donor representation was similar to that observed in similarly-treated recipients of Ly5 congenic marrow, indicating that immunologic alloresistance was completely overcome. These results are consistent with our previous studies demonstrating that the minimal barrier posed by recipient NK cells to allogeneic PHSC engraftment could be readily overcome by administering additional BMC, suggesting that NK cell-mediated resistance is saturable. The observation that greater numbers of allogeneic than syngeneic purified stem cells are required to rescue lethally irradiated mice may reflect a failure to completely overcome T cell-mediated alloresistance. The presence of "facilitating" cell populations in whole marrow inocula is unlikely to have affected our results, since such cell types have generally been reported to express CD4 or CD8, and donor CD4 and CD8 cells are depleted by mAbs present in the circulation at the time of BMT.

clinical stigmata or lymphoid atrophy associated with GVHD probably reflects depletion of mature T cells in donor marrow by mAbs that are still present in the serum at the time of BMT.

To evaluate tolerance, mixed lympyhocyte reactions (MLR) and cell mediated lympholysis (CML) studies were performed in BMT recipients and simultaneous, similarly-treated non-MBT controls 24 to 29 weeks post-conditioning. All four animals with stable multilineage chimerism showed specific CML tolerance to donor and host, with similar anti-third party responses as non-BMT control mice (FIG. 3). The latter group showed similar anti-B10.A responses to those of untreated B6 mice (FIG. 3). Four of six stable chimeras showed donor-specific MLR unresponsiveness, while two animals were generally hyporesponsive. In contrast, all four non-BMT controls showed similar anti-

TABLE 2

Chimerism in B6 recipients of high-dose allogeneic B10.A marrow, anti-CD4 and CD8 mAbs, and 7 Gy TI sacrificed 24 to 29 week post-BMT.

| | | Percentage of donor cells | | | Thymus[a] | |
|---|---|---|---|---|---|---|
| Animal | BMC | CD4 | Spleen CD8 | B Cells | Donor Class I$^{hi}$ | Donor Class II$^{hi}$ |
| B10.A (n = 4) | 92.18 ± 5 | 99.77 ± 0.1 | 99.37 ± 0.6 | 99.76 ± 0.2 | 91.48 ± 6 | + |
| No BMT[b] (n = 4) | 0.06 ± 0.06 | 0 ± 0 | 0 ± 0 | 0.63 ± 0.1 | 0.11 ± 0.2 | − |
| Expt. 1: BMT[c] (200 × 10$^6$ B10.A BMC days 0–4), without TI[d] | | | | | | |
| 1 | ND[a] | 0 | 0.07 | 0.07 | 0 | ND |
| 2 | ND | ND | ND | 0.05 | 0 | ND |
| 3 | 6.98 | 0.47 | 0.25 | 11.29 | ND | ND |
| Expt. 2: BMT[c] (174 × 10$^6$ B10.A BMC days 0–4), with TI | | | | | | |
| Stable | | | | | | |
| Chimeras: 1 | 36.99 | 39.17 | 38.38 | 63.13 | 38.39 | + |
| 2 | 12.38 | 31.14 | 26.71 | 46.32 | 12.27 | ±[f] |
| 3 | 21.90 | 6.32 | 9.86 | 27.69 | 21.83 | + |
| 4 | 45.40 | 35.12 | 31.74 | 55.71 | 24.46 | + |
| 5 | 36.03 | 2.73 | 10.74 | 2.23 | 28.23 | + |
| 6 | 46.63 | 35.24 | 31.58 | 56.89 | 34.20 | + |
| Unstable | | | | | | |
| Chimeras: 1 | 0.33 | 9.10 | 4.15 | 7.43 | 4.95 | − |
| 2 | 12.00 | 19.94 | 17.45 | 40.02 | 6.65 | + |
| 3 | 0.55 | 2.61 | 9.74 | 2.31 | 6.83 | − |

[a]Percentage of total class I$^{high}$, TCRαβ$^{high}$ thymocytes that were of donor type.
[b]These controls were B6 mice that received identical treatment simultaneously with the BMT recipients in Expt. 2, but which did not receive BMT. They received anti-CD4 and CD8 mAbs on days −5, −1 and 7 and 7 Gy TI on day 0.
[c]All animals received anti-CD4 and CD8 mAbs on days −5, −1 and 7.

The mice were evaluated for myelosuppression. Complete blood counts were determined on days −1, 1, 3, 6, 8, 10, 13, and 20 for animals receiving TI on day 0 with or without mAb treatments, without BMT. In recipients of TI±mAbs, average WBC counts reached a nadir of 0.3,000/µl on day 1, and returned to normal by day 8. The lowest level reached in any individual mouse was 2,600/µl. Neither platelet counts nor hemoglobin concentrations decreased significantly at any time in any group. All animals survived with no clinical toxicity. Therefore, host conditioning with mAbs/TI does not cause clinically significant myelosuppression or toxicity, yet permits PGHSC engraftment from high-dose allogeneic marrow.

High-does allogeneic BMT recipients showed no detectable weight loss or other clinical signs of acute or chronic GVHD. The timing of T cell recovery was similar in animals receiving mAbs/TI conditioning with or without high-dose allogeneic BMT, and thymic and splenic cell yields were similar in both groups. The freedom of the recipients from B10.A responses to those of B6 mice (P<0.01 compared to BMT mice). Overall, the results demonstrate donor-specific CML and MLR tolerance in mice receiving high-dose allogeneic BMT with non-myelosuppressive conditioning.

Of two "unstable chimeras" in Table 2, one showed donor-specific CML unresponsiveness and another showed generalized unresponsiveness in CML. Two of the three unstable chimeras showed donor-specific MLR unresponsiveness, while the third showed generalized unresponsiveness (data now shown). The robust responses observed for conditioned non-BMT controls rules out the conditioning regimen itself as the cause of this hyporesponsiveness, and its presence in unstable chimeras, and the lack of evidence for GVHD makes GVH-associated immunodeficiency an unlikely explanation. Cross-reactivity of third party antigens with donor antigens to which the animals were tolerant is the most likely explanation for the weak third party responses in some BMT recipients.

Since some unstable as well as stable chimeras showed donor-specific unresponsiveness in vitro, the decline in chimerism in unstable chimeras may be a more sensitive indicator of incomplete tolerance than MLR or CML. Alternatively, declining chimerism may reflect non-immunologic mechanisms, such as poor PHSC engraftment. To distinguish between these possibilities, tolerance was evaluated by the most stringent test, skin grafting. All stable chimeras permanently accepted donor skin grafts, but rapidly rejected third party grafts, thereby demonstrating donor-specific tolerance (FIG. 4). One unstable chimera in which the declining chimerism was confined to the T cell lineage ("unstable chimera" #2, Table 2) also accepted donor skin. The other two unstable chimeras chronically rejected donor-type skin by days 105 and 48, respectively. In stable chimeras, repeat donor skin grafted 31 weeks post-BMT (and the original grafts) remained in perfect condition until the time of sacrifice three to eight weeks later. Thus, by the most stringent criterion of skin grafting, these animals showed permanent, donor-specific tolerance.

Vβ usage was analysed to examine the mechanism of tolerance in chimeras prepared with high-dose allogeneic marrow. The donor strain, B10.A, expresses I-E, which is required to present Mtv-derived superantigens encoded in the B6/B 10 background genome. Developing thymocytes whose TCR contain Vβ11 or Vβ5, which bind to these superantigens, are deleted in B10.A mice, but not in B6 ($H-2^b$) mice, which do not express I-E (FIG. 5). Vβ11+ and Vβ5+ mature host thymocytes (gated $H-2K^{b\ high}$ cells) and peripheral CD4+ cells were enumerated. Long-term stable chimeras showed deletion of Vβ5 and Vβ11 CD4+ cells among PBL, splenocytes and mature B6 thymocytes, similar to normal B10.A donors. These Vβ were not deleted in non-BMT controls. Percentages of control Vβ8.1/2 cells were normal in all groups (FIG. 5; PBL data not shown). The "unstable chimeras" in Table 2 showed less complete deletion of Vβ5+ and Vβ11+ host-type thymocytes (1.4–4.2% Vβ5, 1.1–5.1% Vβ11) and of CD4 spleen cells and PBL (not shown) than did stable chimeras. Thus, complete deletion of Vβ that recognize donor I-E plus superantigens correlated with the presence of donor-specific skin graft tolerance and permanent, stable mixed chimerism, suggesting that intrathymic deletion was a mechanism of tolerance.

Since hematopoietic cells can efficiently induce clonal deletion in the thymus, we looked for donor I-E in recipient thymi using immunohistochemistry. Donor I-E+ cells were clearly detectable 24 to 29 weeks post-BMT in thymi of most stable chimeras (Table 2). In contrast, two of three unstable chimeras did not contain detectable donor I-E + cells in their thymi (Table 2). Overall, these results demonstrate a correlation between the long-term intrathymic presence of donor-derived class II+ cells and complete deletion of Vβ that recognize superantigens presented by donor MHC molecules. Host class II+ cells were distributed normally in thymi of all recipients. Thymic irradiation was essential to the optimization of stable chimerism (Table 1) and permanent skin graft tolerance. While 7 Gy TI was not significantly myelosuppressive, it permitted high levels PHSC engraftment and permanent, deletional, donor-specific tolerance.

Peripheral chimerism may be achieved through the high doses of bone marrow without the need for whole irradiation. However, to achieve central deletional tolerance it is best to create space in the thymus in order to allow high levels of intrathymic chimerism to develop. This can be achieved by irradiation or by the use of multiple administrations of anti-T cell antibodies or with drugs that deplete the thymus. A level of thymic irradiation between 3 and 7 Gy may be appropriate.

Materials and Methods

Animals

Female C57BL/6 (B6:$H-2^b$), B10.A (B10.A:$H-2^a$, $K^k$, I-$A^k$, I-$E^k$, $D^d$), BALB/c ($H-2^d$), SJL ($H-2^a$) and A.SW ($H-2^a$) mice were purchased from Frederick Cancer Research Center, Frederick, Md., or from The Jackson Laboratory, Bar Harbor, Me. Mice were maintained in a specific pathogen-free microisolator environment.

Conditioning and BMT

Age-matched (7 to 14 weeks old) female B6 recipient mice received 2 mg and 1.4 mg of rat $IgG_{2b}$ anti-mouse CD4 mAb GK 1.5 (Dialynas et al., *J Immunol.* 131:2445–2451 (1983), hereby incorporated by reference) and anti-mouse CD8 mAb 2.43 (Sarmiento *J. Immunol.* 125:2665 (1980), hereby incorporated by reference), respectively, intraperitoneally (i.p.) on days −5, −1 and 7 with respect to BMT. 7 Gy selective thymic irradiation was given on day 0 (Sharabi et al., *J. Exp. Med.* 169:493–502 (1989), hereby incorporated by reference). 35–40×10⁶ untreated BMC from B10.A mice were administered daily on each of days 0 through 4, for a total of five injections (total 174–200×10⁶ BMC).

Mabs

Non-specific FcgR binding was blocked anti-mouse FcgR mAb 2.4G2 (Sherman et al., *Immunogenetics* 12:183–189 (1981), hereby incorporated by reference). FITC-conjugated mAbs included anti-CD4 (Pharmingen, San Diego, Calif.), anti-CD8 (Caltag, San Francisco, Calif. and Pharmingen), anti-MAC1(Caltage) and rat anti-mouse IghM (ymed) mAbs, as well as anti-TCRaβ, -Vb5, -Vb11 and -Vb8.1/2 mAbs purchased from Pharmingen. Negative control mAb HOPC1-FITC, with no reactivity to mouse cells, was prepared in our laboratory. Biotinylated anti-$H-2D^d$ mAb 34-2-12 (Ozato et al., *Transplantation* 34:113–120 (1982), hereby incorporated by reference), anti-$H-2K^b$ mAb 5F1 (Sherman et al., *Immunogenetics* 12:183–189 (1981), hereby incorporated by reference) and control mAb HOPC1 were developed with phycoerythrin-streptavidin (PEA). Phycoerythrin-conjugated anti CD4 mAb (Pharmingen, San Diego, Calif.) and non-specific rat IgG2a (negative control) were purchased from Pharmingen.

Flow cytometric (FCM) analysis of multilineage chimerism

Allogencic reconstitution of various lineages in WBC, spleen marrow and thymus was evaluated by Two-color FCM. Forward angle and 90 degree light scatter properties were used to distinguish lymphocytes, granulocytes and monocytes in WBC, as described. Two-color FCM was utilized to distinguish donor and host cells of particular lineages, an the percentage of donor cells was calculated as described (Lee et al., *Transplantation* 61:125–132 (1996); and Tomita et al., J. Immunol. 153:1087–1098 (1994), both hereby incorporated by reference), by subtracting control staining from quadrants containing donor and host cells of a particular phenotype, and dividing the net percentage of donor cells by the total net percentage of donor plus host cells of that phenotype. Dead cells were excluded by gating out low FSC/high propidium iodide-retaining cells. For analysis of T cell receptor (TCR) Vβ families, $10^4$ gated CD4+ T cells (PBL and spleen) or $10^4$ gated H-2 class $I^{high}$ thymocytes were analyzed as described (Tomita et al., J. Immunol. 153:1087–1098 (1994), hereby incorporated by reference). Class $I^{high}$ thymocytes include mainly mature, single positive T cells (Scollay et al., J. Immunol. 124:2845 (1980), hereby incorporated by reference).

Mixed lymphocyte reactions (MLR)

Splenocytes were cultured in triplicate wells containing 4×10⁵ responders with 4×10⁵ stimulators (30 Gy) in RPMI 1640 medium supplemented with 15% (vol/vol) controlled processed serum replacement (CPSR-2; Sigma), 4% nutrient mixture (7.3 mg/ml L-glutamine, 4×non-essential amino acids (Gibco), 2.75 mg/ml sodium pyruvate, 250 U/ml penicillin and 250 mg/ml streptomycin), 1% Hepes buffer, and 10 mM 2-mercaptoethanol at 37° C. in 5% CO2 for three to four days before they were pulsed with $^3$H-labeled thymidine and harvested 18 hours later. Stimulation index (S.I.) was calculated by comparing anti-donor and anti-third party responses with anti-host responses, which were similar to background counts (i.e., cpm with no stimulator cell population).

Cell-mediated lympholysis (CML) reactions

CML reactions were performed as described (Sykes et al. *J. Immunol.* 140:2903–2911 (1988), hereby incorporated by reference), except that $8 \times 10^5$ responders were cultured with $8 \times 10^5$ stimulators (30 Gy irradiated) in each well, and $8000^{51}$ Cr-labeled 48-hour concanavalin A lymphoblasts were added on day 5.

Skin grafting

Donor-type and third party (SJL) full thickness tail skin grafts were implanted as described (Sharabi et al., *J Exp. Med.* 169:493–502 (1989), hereby incorporated by reference). Grafts were defined as accepted if they were in perfect condition, with tail hairs and scales, and were considered rejected at the time of complete sloughing or when they formed a dry scab.

Immunohistochemistry

Four micron sections were prepared from frozen thymus tissue and stained with mAbs ISCR3 (Watanabe et al., *Transplantation* 36:712–718 (1983), hereby incorporated by reference).(mouse $IgG_{2b}$, anti I-E), 25-9-17 (mouse $IgG_{2a}$ anti-I-A$^b$) (Ozato et al., J. Immunol. 126:317–321 (1981), hereby incorporated by reference), HOPC-1 (mouse $IgG_{2a}$ isotype control) or 74-11-10 (mouse $IgG_{2b}$ isotype control), developed with biotinylated rat anti-mouse $IgG_{2a}$ or anti-$IgG_{2b}$ (Pharmingen), streptavidin-horseradish peroxidates and substrate, as described (Tomita et al., J. Immunol. 153:1087–1098 (1994), hereby incorporated by reference). Stained sections were analyzed by an observer who was unaware of the animal from which the tissue had been obtained.

Statistical analysis

Statistical significance was determined using Student's t-test for comparison of means. A p value of less than 0.05 was considered to be statistically significant.

II. Sources of Cells for Allogeneic Stem Cell Transplantation

A living human donor can provide about $7.5 \times 10^8$ bone marrow cells/kg. Methods of the invention can include the administration of at least 2 or 3 times this number (per kg) and preferably at least 10, 15, or 20 times this number. The requisite numbers of bone marrow cells can be provided by the ex vivo expansion or amplification of human stem cells. Ex vivo expansion is reviewed in Emerson, 1996, Blood 87:3082, hereby incorporated by reference. Methods of ex vivo expansion are described in more detail in Petzer et al., 1996, Proc. Natl. Acad. Sci. USA 93:1470; Zundstra et al., 1994, BioTechnology 12:909; and WO 95 11692 Davis et al., all of which are hereby incorporated by reference. Sources of hematopoietic stem cells include bone marrow cells, mobilized peripheral blood cells, and when available cord blood cells.

Sources of Cells for Xenogeneic Stem Cell Transplantation

In the case of inbred donor animals, e.g., inbred miniature swine, very large numbers of stem cells are available, as the number which can be supplied is not limited by the number which can be harvested from a single donor.

In the case where the recipient is a primate, e.g., a human, and the donor is a swine, e.g., a miniature swine, $7.5 \times 10^9$ or more, and preferably, between $7.5 \times 10^9$ and $15 \times 10^{10}$, swine bone marrow cells/kg can be administered, though this will vary with factors such as the intensity of the preparative regimen and the health of the individual recipient. As discussed herein, these cells can be provided in more than one administrations.

Determination of the Number of Swine Bone Marrow Cells Needed to Induce Tolerance The following system can be used to determine or refine the number of swine cells needed to engraft and induce tolerance in a swine—primate model. Various doses of donor cells are administered to cynomolgus monkeys and the number of cells required for the establishment of chimerism and induction of tolerance determined by the assays described. Time zero is defined as the moment that the arterial and venous cannulas of the recipient are connected to the liver to be perfused.

Thymic space is induced by administering 700 rad of thymic irradiation between days −1 and −8. WBI is not administered.

On day −1 a commercial preparation (Upjohn) of horse anti-human anti-thymocyte globulin (ATG) is injected into the recipient. The recipient is anesthetized, an IV catheter is inserted into the recipient, and 6 ml of heparinized whole blood are removed before infusion. The ATG preparation is then injected (50 mg/kg) intravenously. Six ml samples of heparinized whole blood are drawn for testing at time points of 30 min., 24 hours and 48 hours. Blood samples are analyzed for the effect of antibody treatment on natural killer cell activity (testing on K562 targets) and by FACS analysis for lymphocyte subpopulations, including CD4, CD8, CD3, CD11b, and CD16. If mature T cells and NK cells are not eliminated, ATG can be re-administered at later times in the procedure.

To remove natural antibodies from the recipient's circulation prior to transplantation, on day 0 an operative absorption of natural antibodies (nAB) is performed, using a miniature swine liver, as follows. At −90 minutes the swine donor is anesthetized, And the liver prepared for removal by standard operative procedures. At−60 minutes the recipient monkey is anesthetized. A peripheral IV catheter is inserted, and a 6 ml sample of whole blood is drawn. Through mid-line incision, the abdominal aorta and the vena cava are isolated. Silastic cannulas containing side ports for blood sampling are inserted into the blood vessels.

At −30 minutes the liver is perfused in situ until it turns pale, and then removed from the swine donor and placed into cold Ringers Lactate. The liver is kept cold until just prior to reperfusion in the monkey. A liver biopsy is taken. At −10 minutes the liver is perfused with warm albumin solution until the liver is warm (37 degrees).

At 0 time the arterial and venous cannulas of the recipient are connected to the portal vein and vena cava of the donor liver and perfusion is begun. Liver biopsies are taken at 30 minutes and 60 minutes, respectively. Samples of recipient blood are also drawn for serum at 30 minutes and 60 minutes respectively. At 60 minutes the liver is disconnected from the cannulas and the recipient's large blood vessels are repaired. The liver, having served its function of absorbing harmful natural antibodies from the recipient monkey, is discarded. Additional blood samples for serum are drawn from the recipient at 2, 24, and 48 hours. Organ perfusion can be replaced by perfusion of an α1−3 galactose linkage epitope-affinity matrix, e.g., in the form of an affinity column, e.g., matrix bound linear B type VI carbohydrate.

Swine donor bone marrow cells are administered by intravenous injection. Bone marrow is harvested and injected intravenously as previously described (Pennington et al., 1988, *Transplantation* 45:21–26). $7.5 \times 10^8$/kg bone marrow cells are typically administered in regimens which include WBI. Initial trials to determine an appropriate number of cells to be administered in a regimen which lacks WBI should begin with a range of doses from several times to 20 times that number. Multiple administrations are desirable in the higher end of the dosage range. Swine cytokines can be administered to promote engraftment.

To follow chimerism, two color flow cytometry can be used. This assay uses monoclonal antibodies to distinguish between donor class I major histocompatibility antigens and leukocyte common antigens versus recipient class I major histocompatibility antigens. Alternatively chimerism can be followed by PCR. Should natural antibodies be found to recur before tolerance is induced, and should these antibodies cause damage to the donor tissue, the protocol can be modified to permit sufficient time following BMT for humoral tolerance to be established prior to organ grafting. Tolerance to donor antigen can be followed by standard methods, e.g., by MLR assays.

III. The Induction of Tolerance with Bone Marrow Transplantation

The following procedure was designed to lengthen the time an implanted organ (a xenograft) survives in a xenogeneic host prior to rejection. The organ can be any organ, e.g., a liver, a kidney, a pancreas, or a heart. The method main strategies include one or more of the following: the elimination of natural antibodies, e.g., by contacting the recipient's blood with epitopes which react with donor-reactive natural antibody; inactivation of host T cells; inactivation of host NK cells; transplantation of tolerance-inducing stem cells, e.g., bone marrow stem cells, optionally, the implantation of donor stromal tissue or administration of donor cytokines; and the administration of thymic irradiation. The combination of a sufficiently large number of administered donor stem cells in combination with thymic irradiation significantly reduces or eliminates the need for WBI. The method includes any or all of these steps. Preferably they are carried out in the following sequence.

First, a preparation of horse anti-human thymocyte globulin (ATG) is intravenously injected into the recipient. The antibody preparation eliminates mature T cells and natural killer cells. If not eliminated, mature T cells would promote rejection of both the bone marrow transplant and, after sensitization, the xenograft itself. The ATG preparation also eliminates natural killer (NK) cells. NK cells probably have no effect on the implanted organ, but would act immediately to reject the newly introduced bone marrow. Anti-human ATG obtained from any mammalian host can be used, e.g., ATG produced in pigs, although thus far preparations of pig ATG have been of lower titer than horse-derived ATG. ATG is superior to anti-NK monoclonal antibodies, as the latter are generally not lytic to all host NK cells, while the polyclonal mixture in ATG is capable of lysing all host NK cells. Anti-NK monoclonal antibodies can, however, be used.

The presence of donor antigen in the host thymus during the time when host T cells are regenerating post-transplant is critical for tolerizing host T cells. If donor hematopoietic stem cells are not able to become established in the host thymus and induce tolerance before host T cells regenerate repeated doses of anti-recipient T cell antibodies may be necessary throughout the non-myeloablative regimen. Continuous depletion of host T cells may be required for several weeks.

It may also be necessary or desirable to splenectomize the recipient in order to avoid anemia.

Second, natural antibodies are absorbed from the recipient's blood by hemoperfusion. Pre-formed natural antibodies (nAB) are the primary agents of graft rejection. Natural antibodies bind to xenogeneic endothelial cells. These antibodies are independent of any known previous exposure to antigens of the xenogeneic donor. The mechanism by which newly developing B cells are tolerized is unknown. An $\alpha 1$–$3$ galactose linkage epitope-affinity matrix, e.g., in the form of an affinity column, e.g., matrix bound linear B type VI carbohydrate, is useful for removing anti-swine antibodies from the recipient's blood.

The third step in the non-myeloablative procedure is to supply donor specific growth factors or cytokines, to promote engraftment of donor stem cells.

As liver is the major site of hematopoiesis in the fetus, fetal liver can also serve as an alternative to bone marrow as a source of hematopoietic stem cells. The thymus is the major site of T cell maturation. Each organ includes an organ specific stromal matrix that can support differentiation of the respective undifferentiated stem cells implanted into the host. Although adult thymus may be used, fetal tissue obtained sufficiently early in gestation is preferred because it is free from mature T lymphocytes which can cause GVHD. Fetal tissues also tend to survive better than adult tissues when transplanted. As an added precaution against GVHD, thymic stromal tissue can be irradiated prior to transplantation, e.g., irradiated at 1000 rads. As an alternative or an adjunct to implantation, fetal liver cells can be administered in fluid suspension.

Fourth, bone marrow cells (BMC), or another source of hematopoietic stem cells, e.g., a fetal liver suspension, of the donor are injected into the recipient. Donor BMC home to appropriate sites of the recipient and grow contiguously with remaining host cells and proliferate, forming a chimeric lymphohematopoietic population. By this process, newly forming B cells (and the antibodies they produce) are exposed to donor antigens, so that the transplant will be recognized as self. Tolerance to the donor is also observed at the T cell level in animals in which hematopoietic stem cell, e.g., BMC, engraftment has been achieved. When an organ graft is placed in such a recipient several months after bone marrow chimerism has been induced, natural antibody against the donor will have disappeared, and the graft should be accepted by both the humoral and the cellular arms of the immune system. This approach has the added advantage of permitting organ transplantation to be performed sufficiently long following transplant of hematopoietic cells, e.g., BMT, e.g., a fetal liver suspension, that normal health and immunocompetence will have been restored at the time of organ transplantation. The use of xenogeneic donors allows the possibility of using bone marrow cells and organs from the same animal, or from genetically matched animals.

Many of the methods discussed in the art use whole body irradiation, to create hematopoietic space and thereby promote engraftment. The need for irradiation can be substantially reduced or eliminated by administering a sufficient number of donor bone marrow cells. This should be combined with a treatment, e.g., thymic irradiation, which induces thymic space.

Finally, T cells, particularly, thymic or lymph node T cells, can be further suppressed by administering to the recipient a short course of an immunosuppressive agent, e.g., cyclosporine.

While any of these procedures may aid the survival of an implanted organ, best results are achieved when all steps are used in combination. Methods of the invention can be used to confer tolerance to allogeneic grafts, e.g., wherein both the graft donor and the recipient are humans, and to xenogeneic grafts, e.g., wherein the graft donor is a nonhuman animal, e.g., a swine, e.g., a miniature swine, and the graft recipient is a primate, e.g., a human.

In the case of xenogeneic grafts, the donor of the implant and the individual that supplies either the tolerance-inducing hematopoietic cells or the liver to be perfused should be the same individual or should be as closely related as possible. For example, it is preferable to derive implant tissue from a colony of donors that is highly inbred.

Detailed Protocol

In the following protocol for preparing a cynomolgus monkey for receipt of a kidney from a miniature swine donor, zero time is defined as the moment that the arterial and venous cannulas of the recipient are connected to the liver to be perfused.

On day −1 a commercial preparation (Upjohn) of horse anti-human anti-thymocyte globulin (ATG) is injected into the recipient. ATG eliminates mature T cells and natural killer cells that would otherwise cause rejection of the bone marrow cells used to induce tolerance. The recipient is anesthetized, an IV catheter is inserted into the recipient, and 6 ml of heparinized whole blood are removed before infusion. The ATG preparation is then injected (50 mg/kg) intravenously. Six ml samples of heparinized whole blood are drawn for testing at time points of 30 min., 24 hours and 48 hours. Blood samples are analyzed for the effect of antibody treatment on natural killer cell activity (testing on K562 targets) and by FACS analysis for lymphocyte subpopulations, including CD4, CD8, CD3, CD11b, and CD16. Preliminary data from both assays indicate that both groups of cells are eliminated by the administration of ATG. If mature T cells and NK cells are not eliminated, ATG can be re-administered at later times in the procedure, both before and after organ transplantation.

Sublethal irradiation administered in many art methods is omitted by increasing the number of stem cells administered and by administering 700 rads of thymic irradiation. Thymic irradiation is delivered on day 0.

Natural antibodies are a primary cause of organ rejection. To remove natural antibodies from the recipient's circulation prior to transplantation, on day 0 an operative absorption of natural antibodies (nAB) is performed, using a miniature swine liver, as follows. At −90 minutes the swine donor is anesthetized, And the liver prepared for removal by standard operative procedures. At −60 minutes the recipient monkey is anesthetized. A peripheral IV catheter is inserted, and a 6 ml sample of whole blood is drawn. Through mid-line incision, the abdominal aorta and the vena cava are isolated. Silastic cannulas containing side ports for blood sampling are inserted into the blood vessels.

At −30 minutes the liver is perfused in situ until it turns pale, and then removed from the swine donor and placed into cold Ringers Lactate. The liver is kept cold until just prior to reperfusion in the monkey. A liver biopsy is taken. At −10 minutes the liver is perfused with warm albumin solution until the liver is warm (37 degrees).

At 0 time the arterial and venous cannulas of the recipient are connected to the portal vein and vena cava of the donor liver and perfusion is begun. Liver biopsies are taken at 30 minutes and 60 minutes, respectively. Samples of recipient blood are also drawn for serum at 30 minutes and 60 minutes respectively. At 60 minutes the liver is disconnected from the cannulas and the recipient's large blood vessels are repaired. The liver, having served its function of absorbing harmful natural antibodies from the recipient monkey, is discarded. Additional blood samples for serum are drawn from the recipient at 2, 24, and 48 hours. When this procedure was performed on two sequential perfusions of swine livers, the second liver showed no evidence of mild ischemic changes during perfusion.

To promote long-term survival of the implanted organ through T-cell and B-cell mediated tolerance, donor bone marrow cells are administered to the recipient to form chimeric bone marrow. The presence of donor antigens in the bone marrow allows newly developing B cells, and newly sensitized T cells, to recognize antigens of the donor as self, and thereby induces tolerance for the implanted organ from the donor. To stabilize the donor BMC, donor stromal tissue, in the form of tissue slices of fetal liver, thymus, and/or fetal spleen are transplanted under the kidney capsule of the recipient. Stromal tissue is preferably implanted simultaneously with, or prior to, administration of hematopoietic stem cells, e.g., BMC, or a fetal liver cell suspension. Sufficient stem cells are administered to eliminate the need for preparative or hematopoietic space-creating irradiation.

To follow chimerism, two color flow cytometry can be used. This assay uses monoclonal antibodies to distinguish between donor class I major histocompatibility antigens and leukocyte common antigens versus recipient class I major histocompatibility antigens. BMC can in turn be injected either simultaneously with, or preceding, organ transplant. Bone marrow is harvested and injected intravenously as previously described (Pennington et al., 1988, *Transplantation* 45:21–26). Should natural antibodies be found to recur before tolerance is induced, and should these antibodies cause damage to the graft, the protocol can be modified to permit sufficient time following BMT for humoral tolerance to be established prior to organ grafting.

The approaches described above are designed to synergistically prevent the problem of transplant rejection.

The methods of the invention may be employed in combination, as described, or in part.

The method of introducing bone marrow cells may be altered, particularly by (1) increasing the time interval between injecting hematopoietic stem cells and implanting the graft; (2) increasing the amount of hematopoietic stem cells injected; (3) varying the number of hematopoietic stem cell injections; (4) varying the method of delivery of hematopoietic stem cells; (5) varying the tissue source of hematopoietic stem cells, e.g., a fetal liver cell suspension may be used; or (6) varying the donor source of hematopoietic stem cells. Although hematopoietic stem cells derived from the graft donor are preferable, hematopoietic stem cells may be obtained from other individuals or species, or from genetically-engineered inbred donor strains, or from in vitro cell culture.

Methods of preparing the recipient for transplant of hematopoietic stem cells may be varied. For instance, recipient may undergo a splenectomy. The latter would preferably be administered prior to the non-myeloablative regimen, e.g., at day −14.

Hemoperfusion of natural antibodies may: (1) make use of other vascular organs, e.g., liver, kidney, intestines; (2) make use of multiple sequential organs or affinity matrices; (3) vary the length of time each organ or affinity matrices is perfused; (4) vary the donor of the perfused organ. Antibodies introduced prior to hematopoietic cell transplant may be varied by: (1) using monoclonal antibodies to T cell subsets or NK cells (e.g., anti-NKHIA, as described by U.S. Pat. No. 4,772,552 to Hercend, et al., hereby incorporated by reference); (2) preparing anti-human ATG in other mammalian hosts (e.g., monkey, pig, rabbit, dog); or (3) using anti-monkey ATG prepared in any of the above mentioned hosts.

The methods of the invention may be employed with other mammalian recipients (e.g., rhesus monkeys) and may use other mammalian donors (e.g., primates, sheep, or dogs). As an alternative or adjunct to hemoperfusion, host antibodies can be depleted by administration of an excess of hematopoietic cells.

Stromal tissue introduced prior to hematopoietic cell transplant, e.g., BMT, may be varied by: (1) administering the fetal liver and thymus tissue as a fluid cell suspension; (2) administering fetal liver or thymus stromal tissue but not both; (3) placing a stromal implant into other encapsulated, well-vascularized sites, or (4) using adult thymus or fetal spleen as a source of stromal tissue.

Other Embodiments

The methods described herein for inducing tolerance to, or promoting the acceptance of, an allogeneic antigen or allogeneic graft can be used where, as between the donor and recipient, there is any degree of mismatch at MHC loci or other loci which influence graft rejection. Preferably, there is a mismatch at least one MHC locus or at at least one other locus that mediates recognition and rejection, e.g., a minor antigen locus. With respect to class I and class II MHC loci, the donor and recipient can be: matched at class I and mismatched at class II; mismatched at class I and matched at class II; mismatched at class I and mismatched at class II; matched at class I, matched at class II. In any of these combinations other loci which control recognition and rejection, e.g., minor antigen loci, can be matched or mismatched. As stated above, it is preferable that there is mismatch at least one locus. Mismatched at MHC class I means mismatched for one or more MHC class I loci, e.g., in the case of humans, mismatched at one or more of HLA-A, HLA-B, or HLA-C, or in the case of swine, mismatch at one or more SLA class I loci, e.g., the swine A or B loci. Mismatched at MHC class II means mismatched at one or more MHC class II loci, e.g., in the case of humans, mismatched at one or more of a DP α, a DPβ, a DQ α, a DQ β, a DR α, or a DR β, or in the case of swine, mismatch at one or SLA class II loci, e.g., mismatch at DQ α or β, or DR α or β.

The methods described herein for inducing tolerance to an allogeneic antigen or allogeneic graft can be used where, as between the donor and recipient, there is any degree of reactivity in a mixed lymphocyte assay, e.g., wherein there is no, low, intermediate, or high mixed lymphocyte reactivity between the donor and the recipient. In preferred embodiments mixed lymphocyte reactivity is used to define mismatch for class II, and the invention includes methods for performing allogeneic grafts between individuals with any degree of mismatch at class II as defined by a mixed lymphocyte assay. Serological tests can be used to determine mismatch at class I or II loci and the invention includes methods for performing allogeneic grafts between individuals with any degree of mismatch at class I and or II as measured with serological methods. In a preferred embodiment, the invention features methods for performing allogeneic grafts between individuals which, as determined by serological and or mixed lymphocyte reactivity assay, are mismatched at both class I and class II.

The methods of the invention are particularly useful for replacing a tissue or organ afflicted with a neoplastic disorder, particularly a disorder which is resistant to normal modes of therapy, e.g., chemotherapy or radiation therapy. Methods of the invention can be used for inducing tolerance to a graft, e.g., an allograft, e.g., an allograft from a donor which is mismatched at one or more class I loci, at one or more class II loci, or at one or more loci at each of class I and class II. In preferred embodiments: the graft includes tissue from the digestive tract or gut, e.g., tissue from the stomach, or bowel tissue, e.g., small intestine, large intestine, or colon; the graft replaces a portion of the recipient's digestive system e.g., all or part of any of the digestive tract or gut, e.g., the stomach, bowel, e.g., small intestine, large intestine, or colon.

Methods of the invention minimize or eliminate the need for preparative WB irradiation. However, when irradiation is administered, it is possible to induce mixed chimerism with less radiation toxicity by fractionating the radiation dose, i.e., by delivering the radiation in two or more exposures or sessions. Accordingly, in any method of the invention calling for the irradiation of a recipient, e.g., a primate, e.g., a human, recipient, of a xenograft or allograft, the radiation can either be delivered in a single exposure, or more preferably, can be fractionated into two or more exposures or sessions. The sum of the fractionated dosages is preferably equal, e.g., in rads or Gy, to the radiation dosage which can result in mixed chimerism when given in a single exposure. The fractions are preferably approximately equal in dosage. Hyperfractionation of the radiation dose can also be used in methods of the invention. The fractions can be delivered on the same day, or can be separated by intervals of one, two, three, four, five, or more days. Whole body irradiation, thymic irradiation, or both, can be fractionated.

Thymic irradiation can also be fractionated. For example, a single dose of 700 rads can be replaced with, e.g., two fractions of 350 rads, or seven fractions of 100 rads.

Methods of the invention can include recipient splenectomy.

As is discussed herein, hemoperfusion, e.g., hemoperfusion with a donor organ, can be used to deplete the host of natural antibodies. Other methods for depleting or otherwise inactivating natural antibodies can be used with any of the methods described herein. For example, drugs which deplete or inactivate natural antibodies, e.g., deoxyspergualin (DSG) (Bristol), or anti-IgM antibodies, can be administered to the recipient of an allograft or a xenograft. One or more of, DSG (or similar drugs), anti-IgM antibodies, and hemoperfusion, can be used to deplete or otherwise inactivate recipient natural antibodies in methods of the invention. DSG at a concentration of 6 mg/kg/day, i.v., has been found useful in suppressing natural antibody function in pig to cynomolgus kidney transplants.

In any of the methods described herein, particularly primate or clinical methods, it is preferable to form mixed chimerism as opposed to entirely replacing the recipient's stem cells with donor cells.

Alternative methods for the inactivation of thymic T cells are also included in embodiments of the invention. Some of the methods described herein include the administration of thymic irradiation to inactivate host thymic-T cells or to otherwise diminish the host's thymic-T cell mediated responses to donor antigens. It has been discovered that the thymic irradiation called for in allogeneic or xenogeneic methods of the invention can be supplemented with, or replaced by, other treatments which diminish (e.g., by depleting thymic-T cells and/or down modulating one or more of the T cell receptor (TCR), CD4 co-receptor, or CD8 co-receptor) the host's thymic-T cell mediated response. For example, thymic irradiation can be supplemented with, or replaced by, anti-T cell antibodies (e.g., anti-CD4 and/or anti-CD8 monoclonal antibodies) administered a sufficient number of times, in sufficient dosage, for a sufficient period of time, to diminish the host's thymic-T cell mediated response.

For best results, anti-T cell antibodies should be administered repeatedly. E.g., anti-T cell antibodies can be administered one, two, three, or more times prior to donor bone marrow transplantation. Typically, a pre-bone marrow transplantation dose of antibodies will be given to the patient about 5 days prior to bone marrow transplantation. Additional, earlier doses 6, 7, or 8 days prior to bone marrow transplantation can also be given. It may be desirable to administer a first treatment then to repeat pre-bone marrow administrations every 1–5 days until the patient shows excess antibodies in the serum and about 99% depletion of peripheral T cells and then to perform the bone marrow transplantation. Anti-T cell antibodies can also be administered one, two, three, or more times after donor bone marrow transplantation. Typically, a post-bone marrow transplant treatment will be given about 2–14 days after bone marrow transplantation. The post bone marrow administration can be repeated as many times as needed. If more than one administration is given the administrations can be spaced about 1 week apart. Additional doses can be given if the patient appears to undergo early or unwanted T cell recovery. Preferably, anti-T cell antibodies are administered at least once (and preferably two, three, or more times) prior to donor bone marrow transplantation and at least once (and preferably two, three, or more times) after donor bone marrow transplantation.

Some of the methods herein include the administration of hematopoietic stem cells to a recipient. In many of those methods, hematopoietic stem cells are administered prior to or at the time of the implantation of a graft (an allograft or a xenograft), the primary purpose of the administration of hematopoietic stem cells being the induction of tolerance to the graft. The inventors have found that one or more subsequent administrations (e.g., a second, third, fourth, fifth, or further subsequent administration) of hematopoietic stem cells can be desirable in the creation and/or maintenance of tolerance. Thus, the invention also includes methods in which hematopoietic stem cells are administered to a recipient, e.g., a primate, e.g., a human, which has previously been administered hematopoietic stem cells as part of any of the methods referred to herein.

While not wishing to be bound by theory the inventor believes that repeated stem cell administration may promote chimerism and possibly long-term deletional tolerance in graft recipients. Accordingly, any method referred to herein which includes the administration of hematopoietic stem cells can further include multiple administrations of stem cells. In preferred embodiments: a first and a second administration of stem cells are provided prior to the implantation of a graft; a first administration of stem cells is provided prior to the implantation of a graft and a second administration of stem cells is provided at the time of implantation of the graft. In other preferred embodiments: a first administration of stem cells is provided prior to or at the time of implantation of a graft and a second administration of stem cells is provided subsequent to the implantation of a graft. The period between administrations of hematopoietic stem cells can be varied. In preferred embodiments a subsequent administration of hematopoietic stem cell is provided: at least two days, one week, one month, or six months after the previous administration of stem cells; at least two days, one week, one month, or six months after the implantation of the graft.

The method can further include the step of administering a second or subsequent dose of hematopoietic stem cells: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's , e.g. when the donor specific monoclonal stains less than 1–2% of the cells; or generally, as is needed to maintain tolerance or otherwise prolong the acceptance of a graft. Thus, method of the invention can be modified to include a further step of determining if a subject which has received a one or more administrations of hematopoietic stem cells is in need of a subsequent administration of hematopoietic stem cells, and if so, administering a subsequent dose of hematopoietic stem cells to the recipient.

Any of the methods referred to herein can include the administration of agents, e.g., 15-deoxyspergualin, mycophenolate mofetil, brequinar sodium, or similar agents, which inhibit the production, levels, or activity of antibodies in the recipient. One or more of these agents can be administered: prior to the implantation of donor tissue, e.g., one, two, or three days, or one, two, or three weeks before implantation of donor tissue; at the time of implantation of donor tissue; or after implantation of donor tissue, e.g., one, two, or three days, or one, two or three weeks after, implantation of a graft.

The administration of the agent can be initiated: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's , e.g. when the donor specific monoclonal stains less than 1–2 % of the cells; or generally, as is needed to maintain tolerance or otherwise prolong the acceptance of a graft.

The period over which the agent is administered (or the period over which clinically effective levels are maintained in the subject) can be long term, e.g., for six months or more or a year or more, or short term, e.g., for less than a year, more preferably six months or less, more preferably one month or less, and more preferably two weeks or less. The period will generally be at least about one week and preferably at least about two weeks in duration. In preferred embodiments the period is two or three weeks long.

Preferred embodiments include administration of 15-deoxyspergualin (6 mg/kg/day) for about two weeks beginning on the day of graft implantation.

Some of the methods referred to herein include the administration of hematopoietic stem cells to a recipient. The inventors have found that administration of one or more cytokines, preferably a cytokine from the species from which the stem cells are derived, can promote engraftment, mixed chimerism, and tolerance, or otherwise prolong acceptance of a graft. The use of such cytokines can reduce or eliminate the need for whole body irradiation. Thus, the invention also includes methods in the recipient is administered one or more cytokine, e.g., a donor-species cytokine.

Although not wishing to be bound by theory, the inventors believe that the cytokines, particularly donor species cytokines, promote the engraftment and/or function of donor stem cells or their progeny cells. Accordingly, any method referred to herein which includes the administration of hematopoietic stem cells can further include the administration of a cytokine, e.g., SCF, IL-3, or GM-CSF. In preferred embodiments the cytokine one which is species specific in its interaction with target cells.

Administration of a cytokine can begin prior to, at, or after the implantation of a graft or the implantation of stem cells.

The method can further include the step of administering a first or subsequent dose of a cytokine to the recipient: when the recipient begins to show signs of rejection, e.g., as evidenced by a decline in function of the grafted organ, by a change in the host donor specific antibody response, or by a change in the host lymphocyte response to donor antigen; when the level of chimerism decreases; when the level of chimerism falls below a predetermined value; when the level of chimerism reaches or falls below a level where staining with a monoclonal antibody specific for a donor PBMC antigen is equal to or falls below staining with an isotype control which does not bind to PBMC's, e.g. when the donor specific monoclonal stains less than 1–2% of the cells; or generally, as is needed to maintain tolerance or otherwise prolong the acceptance of a graft. Thus, method of the invention can be modified to include a further step of determining if a subject is in need of cytokine therapy and if so, administering a cytokine.

The period over which the cytokine(s) is administered (or the period over which clinically effective levels are maintained in the subject) can be long term, e.g., , for six months of more or a year or more, or short term, e.g., for a year or less, more preferably six months or less, more preferably one month or less, and more preferably two weeks or less. The period will generally be at least about one week and preferably at least about two weeks in duration.

In preferred embodiments the recipient is a primate, e.g., a human, and the donor is from a different species, e.g., the donor is a pig and: pig SCF is administered; pig IL-3 is administered; a combination of pig SCF and pig IL-3 is administered; a pig specific hematopoiesis enhancing factor, e.g., pig GM-SCF, is administered, e.g., after the implantation of stem cells, e.g., about a month after the implantation of stem cells.

A particularly preferred embodiment combines a short course, e.g., about a month, of cyclosporine or a similar agent, a short course, e.g., about two weeks, of 15-deoxyspergualin or a similar agent, and a short course, e.g., about two weeks, of donor specific cytokines, e.g., SCF and IL-3. In Cynomolgus monkeys receiving pig grafts and pig stem cells, treatment which included the combination of cyclosporine (15 mg/kg/day for 28 days), 15-deoxyspergualin (6 mg/kg/day for two weeks), and recombinant pig cytokines (SCF and IL-3, each at 10 µg/kg/day, i.v., for two weeks) was found to be useful. Administration began at the time of graft implant. (The monkeys were also given a preparative regime consisting of 3×100cGy whole body irradiation on day −6, and −5 and hemoperfusion with a pig liver just prior to stem cell administration.) An anti-CD2 antibody, preferably a monoclonal, e.g., BTI-322, or a monoclonal directed at a similar or overlapping epitope, can be used in addition to or in place of any anti-T cell antibodies (e.g., ATG) in any method referred to herein.

Other embodiments are within the following claims.

What is claimed is:

1. A method of promoting, tolerance in a recipient mammal of a first species, to a graft obtained from a donor mammal of a second species comprising:

introducing into said recipient mammal, hematopoietic stem cells of said second species;

creating thymic space in said recipient; and introducing said graft into said recipient, wherein the number of donor stem cells administered is sufficient such that mixed chimerism can be formed without hematopoietic space-creating irradiation.

2. The method of claim 1, wherein said mixed chimerism is formed in the absence of hematopoietic space created by whole body irradiation.

3. The method of claim 1, wherein said recipient is a human.

4. The method of claim 1, wherein said recipient is a human and said graft is from a swine.

5. The method of claim 4, wherein said swine is a miniature swine.

6. The method of claim 1, wherein said thymic space is created by one or more of the following, by administering thymic irradiation, steroids, corticosteroids, brequinar, or an immune suppressant chemical or drug to the recipient.

7. The method of claim 1, wherein said thymic space is created by administering thymic irradiation, to said recipient.

8. The method of claim 1, wherein said thymic space is created by administering an immune suppressant chemical or drug to said recipient.

9. The method of claim 1, wherein said thymic space is created by administering a short course of cyclosporin to said recipient.

10. The method of claim 1, wherein multiple hematopoietic stem cell administrations are provided to said recipient.

11. The method of claim 1, further comprising inactivating donor-reactive T cells of said recipient mammal.

12. The method of claim 1, further comprising inactivating donor-reactive NK cells of said recipient mammal.

13. The method of claim 1, wherein said graft comprises a kidney.

14. The method of claim 1, wherein said graft comprises a liver.

15. A method of inducing tolerance in a recipient mammal to an allogeneic graft obtained from a donor mammal of the same species without hematopoietic space-creating irradiation comprising:

introducing into said recipient mammal, hematopoietic stem cells of said donor;

creating thymic space in said recipient; and implanting said graft in said recipient, wherein the number of donor stem cells administered is sufficient such that mixed chimerism can be formed without hematopoietic space-creating irradiation.

16. The method of claim 15, wherein said mixed chimerism is formed in the absence of hematopoietic space created by whole body irradiation.

17. The method of claim 15, wherein said recipient is a human.

18. The method of claim 15, wherein said thymic space is created by one or more of the following, by administering thymic irradiation, steroids, corticosteroids, brequinar, or an immune suppressant chemical or drug to the recipient.

19. The method of claim 15, wherein said thymic space is created by administering thymic irradiation to said recipient.

20. The method of claim 15, wherein said thymic space is created by administering an immune suppressant chemical or drug to the recipient.

21. The method of claim 15, wherein said thymic space is created by administering a short course of cyclosporin to said recipient.

22. The method of claim 15, wherein multiple hematopoietic stem cell administrations are provided to said recipient.

23. The method of claim 15, further comprising inactivating donor-reactive T cells of said recipient mammal.

24. The method of claim 15, further comprising inactivating donor-reactive NK cells of said recipient mammal.

25. The method of claim 15, wherein said graft comprises a kidney.

26. The method of claim 15, wherein said graft comprises a liver.

27. The method of claim 15, wherein the number of donor hematopoietic cells administered is at least 25% as great as the number of bone marrow cells found in an adult of the recipient species.

28. The method of claim 15, wherein the number of donor hematopoietic cells administered is at least 50% as great as the number of bone marrow cells found in an adult of the recipient species.

29. The method of claim 15, wherein the number of donor hematopoietic cells administered is at least 75% as great as the number of bone marrow cells found in an adult of the recipient species.

30. The method of claim 15, wherein the number of donor hematopoietic cells administered is at least as great as the number of bone marrow cells found in an adult of the recipient species.

31. The method of claim 15, wherein the number of donor hematopoietic cells administered is at least twice as great as the number of bone marrow cells found in an adult of the recipient species.

32. The method of claim 15, wherein the number of donor hematopoietic stem cells administered is at least 25% as great as the number of bone marrow hematopoietic stem cells found in an adult of the recipient species.

33. The method of claim 15, wherein the number of donor hematopoietic stem cells administered is at least 50% as great as the number of bone marrow hematopoietic stem cells found in an adult of the recipient species.

34. The method of claim 15, wherein the number of donor hematopoietic stem cells administered is at least 75% as great as the number of bone marrow hematopoietic stem cells found in an adult of the recipient species.

35. The method of claim 15, wherein the number of donor hematopoietic stem cells administered is at least as great as the number of bone marrow hematopoietic stem cells found in an adult of the recipient species.

36. The method of claim 15, wherein the number of donor hematopoietic stem cells administered is at least twice as great as the number of bone marrow hematopoietic stem cells found in an adult of the recipient species.

37. A method of inducing tolerance in a recipient mammal to an allogeneic graft obtained from a donor mammal of the same species without hematopoietic space-creating irradiation comprising:

introducing into said recipient mammal, hematopoietic stem cells of said donor;

administering thymic irradiation to create thymic space in said recipient; and implanting said graft in said recipient, wherein the number of donor stem cells administered is sufficient such that mixed chimerism can be formed without hematopoietic space-creating irradiation.

38. The method of claim 37, wherein said recipient is a human.

39. The method of claim 37, wherein multiple hematopoietic stem cell administrations are provided to said recipient.

40. The method of claim 37, further comprising inactivating donor-reactive T cells of said recipient mammal.

41. The method of claim 37, further comprising inactivating donor-reactive NK cells of said recipient mammal.

42. The method of claim 37, wherein said graft comprises a kidney.

43. The method of claim 37, wherein said graft comprises a liver.

44. The method of claim 37, wherein the number of donor hematopoietic cells administered is at least 25% as great as the number of bone marrow cells found in an adult of the recipient species.

45. The method of claim 37, wherein the number of donor hematopoietic cells administered is at least 50% as great as the number of bone marrow cells found in an adult of the recipient species.

46. The method of claim 37, wherein the number of donor hematopoietic cells administered is at least 75% as great as the number of bone marrow cells found in an adult of the recipient species.

47. The method of claim 37, wherein the number of donor hematopoietic cells administered is at least as great as the number of bone marrow cells found in an adult of the recipient species.

48. The method of claim 37, wherein the number of donor hematopoietic cells administered is at least twice as great as the number of bone marrow cells found in an adult of the recipient species.

49. The method of claim 37, wherein the number of donor hematopoietic stem cells administered is at least 25% as great as the number of bone marrow hematopoietic stem cells found in an adult of the recipient species.

50. The method of claim 37, wherein the number of donor hematopoietic stem cells administered is at least 50% as great as the number of bone marrow hematopoietic stem cells found in an adult of the recipient species.

51. The method of claim 37, wherein the number of donor hematopoietic stem cells administered is at least 75% as great as the number of bone marrow hematopoietic stem cells found in an adult of the recipient species.

52. The method of claim 37, wherein the number of donor hematopoietic stem cells administered is at least as great as the number of bone marrow hematopoietic stem cells found in an adult of the recipient species.

53. The method of claim 37, wherein the number of donor hematopoietic stem cells administered is at least twice as great as the number of bone marrow hematopoietic stem cells found in an adult of the recipient species.

* * * * *